(12) United States Patent
Bally

(10) Patent No.: US 9,816,663 B2
(45) Date of Patent: Nov. 14, 2017

(54) SECURE EQUIPMENT TRANSFER SYSTEM

(71) Applicant: Nexxspan Healthcare, LLC, Lithia, FL (US)

(72) Inventor: Alexander Bally, Marston Mills, MA (US)

(73) Assignee: Nexxspan Healthcare, LLC, Lithia, FL (US)

( * ) Notice: Subject to any disclaimer, the term of this patent is extended or adjusted under 35 U.S.C. 154(b) by 0 days.

(21) Appl. No.: 15/019,323

(22) Filed: Feb. 9, 2016

(65) Prior Publication Data

US 2016/0153611 A1 Jun. 2, 2016

Related U.S. Application Data

(63) Continuation of application No. 14/064,345, filed on Oct. 28, 2013, now Pat. No. 9,404,616, which is a (Continued)

(51) Int. Cl.
*A61G 7/10* (2006.01)
*F16M 13/00* (2006.01)
(Continued)

(52) U.S. Cl.
CPC ............ *F16M 13/00* (2013.01); *A61G 7/012* (2013.01); *A61G 12/005* (2013.01); *A61M 5/1417* (2013.01); *F16M 13/02* (2013.01); *A61G 7/0015* (2013.01); *A61G 7/0506* (2013.01); *A61G 7/1025* (2013.01); *A61G 7/1073* (2013.01);
(Continued)

(58) Field of Classification Search
CPC ................ A61G 12/005; A61G 12/008; A61G 2203/80; A61G 7/012; A61G 7/015; A61G 7/1025; A61G 7/1055; A61G 7/1057; A61G 7/1073; A61F 5/045; A61M 5/1415; F16M 2200/02; F16M 13/02

USPC .......... 248/276.1, 287.1, 288.51, 125.7, 314, 248/158, 176.1; 5/503.1, 658; 414/343,
(Continued)

(56) References Cited

U.S. PATENT DOCUMENTS 2,409,432 A 10/1946 Hubbard
2,460,244 A 1/1949 Strauss
(Continued)

FOREIGN PATENT DOCUMENTS

NL 2000571 10/2008
WO 2017147005 8/2017

OTHER PUBLICATIONS

Bally, Alexander; Issue Notification for U.S. Appl. No. 14/064,345, filed Oct. 28, 2013, dated Jul. 13, 2016, 1 pg.
(Continued)

*Primary Examiner* — Tan Le
(74) *Attorney, Agent, or Firm* — Taylor English Duma LLP

(57) ABSTRACT

A method of using a transfer system includes: supporting a first docking cone of the transfer system by a first support platform to orient a docking cone axis of the first docking cone with a vertical axis; inserting the first docking cone into a first docking cup of a transfer device of the transfer system; and locking the first docking cone within the first docking cup by a security mechanism of the transfer device, the security mechanism comprising a first security lever and a second security lever.

19 Claims, 45 Drawing Sheets

Related U.S. Application Data continuation-in-part of application No. 13/104,531, filed on May 10, 2011, now Pat. No. 8,579,244.

(60) Provisional application No. 61/332,918, filed on May 10, 2010.

(51) Int. Cl.

| | | |
|---|---|---|
| *A61G 12/00* | (2006.01) | |
| *A61G 7/012* | (2006.01) | |
| *F16M 13/02* | (2006.01) | |
| A61G 7/00 | (2006.01) | |
| A61G 7/05 | (2006.01) | |
| A61M 5/14 | (2006.01) | |

(52) U.S. Cl.
CPC ....... *A61G 2203/80* (2013.01); *A61M 5/1415* (2013.01)

(58) Field of Classification Search
USPC ..... 414/349; 403/121, 322.1, 325, 326, 334, 403/12
See application file for complete search history.

(56) References Cited

U.S. PATENT DOCUMENTS

| | | |
|---|---|---|
| 3,570,376 A | 3/1971 | Overton |
| 3,912,405 A | 10/1975 | Katt |
| D262,237 S | 12/1981 | Stauber |
| 4,511,158 A | 4/1985 | Varga et al. |
| 4,945,592 A | 8/1990 | Sims et al. |
| D339,195 S | 9/1993 | Nash et al. |
| 5,306,109 A | 4/1994 | Kreuzer et al. |
| 5,366,191 A | 11/1994 | Bekanich |
| 5,474,408 A | 12/1995 | Dinitz |
| 5,527,125 A | 6/1996 | Kreuzer et al. |
| D381,745 S | 7/1997 | Owens |
| 5,898,961 A | 5/1999 | Ambach et al. |
| 6,042,292 A | 3/2000 | Belanger |
| 7,065,812 B2 | 6/2006 | Newkirk et al. |
| 7,254,850 B2 | 8/2007 | Newkirk et al. |
| 7,258,310 B2 | 8/2007 | Norris |
| 7,314,200 B2 | 1/2008 | Bally |
| 7,418,749 B2 | 9/2008 | Graham et al. |
| 7,661,641 B2 | 2/2010 | Wong et al. |
| 7,676,865 B2 | 3/2010 | Graham et al. |
| 7,735,788 B2 | 6/2010 | Newkirk et al. |
| 7,748,672 B2 | 7/2010 | Walke |
| 7,789,361 B2 | 9/2010 | Bally et al. |
| 7,798,456 B2 | 9/2010 | Newkirk et al. |
| 7,845,601 B1 | 12/2010 | Culpepper et al. |
| 7,865,983 B2 | 1/2011 | Newkirk et al. |
| 7,980,533 B1 | 7/2011 | Anderson |
| 8,104,729 B2 | 1/2012 | Walke et al. |
| D655,408 S | 3/2012 | Bally |
| D655,409 S | 3/2012 | Bally |
| 8,579,244 B2 * | 11/2013 | Bally .................. A61G 7/1025 248/224.7 |
| 9,404,616 B2 * | 8/2016 | Bally .................... F16M 13/00 |
| 9,528,536 B2 | 12/2016 | Bally |
| 2005/0253034 A1 | 11/2005 | Bally et al. |
| 2006/0179571 A1 | 8/2006 | Newkirk |
| 2006/0242763 A1 | 11/2006 | Graham et al. |
| 2006/0249641 A1 | 11/2006 | Bally et al. |
| 2007/0069093 A1 | 3/2007 | Graham et al. |
| 2007/0157385 A1 | 7/2007 | Lemire |
| 2007/0267550 A1 | 11/2007 | Blankenship et al. |
| 2008/0149788 A1 | 6/2008 | Wong et al. |
| 2008/0217910 A1 | 9/2008 | Walke et al. |
| 2009/0065668 A1 | 3/2009 | Walke |
| 2011/0217876 A1 | 9/2011 | Siebens |
| 2011/0272538 A1 | 11/2011 | Bally |
| 2013/0125367 A1 | 5/2013 | Rode |
| 2014/0048661 A1 | 2/2014 | Bally |
| 2014/0237721 A1 | 8/2014 | Lemire |
| 2016/0153611 A1 * | 6/2016 | Bally .................... F16M 13/00 248/221.11 |
| 2017/0049525 A1 | 2/2017 | Bally |
| 2017/0241457 A1 | 8/2017 | Bally |
| 2017/0241461 A1 | 8/2017 | Bally |

OTHER PUBLICATIONS

Bally, Alexander; Advisory Action for U.S. Appl. No. 14/686,439, filed Apr. 14, 2015, dated Jul. 11, 2016, 3 pgs.

Bally, Alexander; Applicant Initiated Interview Summary for U.S. Appl. No. 14/686,439, filed Apr. 14, 2015, dated Jun. 17, 2016, 3 pgs.

Bally, Alex; International Preliminary Report on Patentability for PCT/US2013/067007, filed Oct. 28, 2013, dated May 3, 2016, 6 pgs.

Bally, Alexander; Issue Notification for U.S. Appl. No. 13/104,531, filed May 10, 2011, dated Oct. 23, 2013, 1 pg.

Bally, Alexander; Non-Final Office Action for U.S. Appl. No. 13/104,531, filed May 10, 2011, dated Apr. 23, 2013, 15 pgs.

Bally, Alexander; Notice of Allowance for U.S. Appl. No. 13/104,531, filed May 10, 2011, dated Aug. 22, 2013, 12 pgs.

Bally, Alexander; Restriction Requirement for U.S. Appl. No. 13/104,531, filed May 10, 2011, dated Feb. 5, 2013, 6 pgs.

Bally, Alexander; U.S. Patent Application entitled: Secure Equipment Transfer System, having U.S. Appl. No. 13/104,531, filed May 10, 2011, 81 pgs.

Bally, Alexander; Final Office Action for U.S. Appl. No. 14/064,345, filed Oct. 28, 2013, dated Jul. 15, 2015, 9 pgs.

Bally, Alexander; Non-Final Office Action for U.S. Appl. No. 14/064,345, filed Oct. 28, 2013, dated Apr. 6, 2015, 14 pgs.

Bally, Alexander; Notice of Allowance for U.S. Appl. No. 14/064,345, filed Oct. 28, 2013, dated Nov. 9, 2015, 10 pgs.

Bally, Alexander; U.S. Continuation Application entitled: Secure Equipment Transfer System, having U.S. Appl. No. 14/064,345, filed Oct. 28, 2013, 89 pgs.

Bally, Alexander; Applicant-Initiated Interview Summary for U.S. Appl. No. 14/686,439, filed Apr. 14, 2015, dated Oct. 22, 2015, 3 pgs.

Bally, Alexander; Non-Final Office Action for U.S. Appl. No. 14/686,439, filed Apr. 14, 2015, dated Sep. 1, 2015, 20 pgs.

Bally, Alexander; U.S. Patent Application entitled: Secure Equipment Transfer System having U.S. Appl. No. 14/686,439, filed Apr. 14, 2015, 124 pgs.

Bally, Alexander; International Search Report and Written Opinion for PCT/US2013/067007, filed Oct. 28, 2013, dated Mar. 10, 2014, 8 pgs.

Bally, Alexander; PCT Application entitled: Secure Equipment Transfer System, having serial No. PCT/US2013/067007, filed Oct. 28, 2013, 71 pgs.

Bally, Alexander; International Search Report and Written Opinion for PCT Application No. PCT/US15/27300, filed Apr. 23, 2015, dated Sep. 1, 2015, 13 pgs.

Bally, Alexander; PCT Application entitled: Secure Equipment Transfer System having serial No. PCT/US15/27300, filed Apr. 23, 2015, 125 pgs.

Bally, Alexander; Issue Notification for U.S. Appl. No. 29/393,210, filed Jun. 1, 2011, dated Feb. 15, 2012, 1 pg.

Bally, Alexander; Non-Final Office Action for U.S. Appl. No. 29/393,210, filed Jun. 1, 2011, dated Oct. 26, 2011, 7 pgs.

Bally, Alexander; Notice of Allowance for U.S. Appl. No. 29/393,210, filed Jun. 1, 2011, dated Nov. 23, 2011, 5 pgs.

Bally, Alexander; U.S. Design Application entitled: Symmetrical Transfer Device, having U.S. Appl. No. 29/393,210, filed May 1, 2011, 8 pgs.

Bally, Alexander; Issue Notification for U.S. Appl. No. 29/393,211, filed Jun. 1, 2011, dated Feb. 15, 2012, 1 pg.

Bally, Alexander; Non-Final Office Action for U.S. Appl. No. 29/393,211, filed Jun. 1, 2011, dated Oct. 25, 2011, 6 pgs.

Bally, Alexander; Notice of Allowance for U.S. Appl. No. 29/393,211, filed Jun. 1, 2011, dated Nov. 25, 2011, 5 pgs.

(56) References Cited

OTHER PUBLICATIONS

Bally, Alexander; U.S. Design Application entitled: Asymetrical Transfer Device, having U.S. Appl. No. 29/393,211, filed Jun. 1, 2011, 8 pgs.

Bally, Alexander; U.S. Provisional Patent Application Entitled: Secure Equipment Transfer System, U.S. Appl. No. 61/332,918, filed May 10, 2010; 63 pgs.

IMEC-TRUMPF North America, article located at <www.us.trumpf.com/products/,,,/imec.html>, accessed on Sep. 1, 2010, 1 pg.

Bally, Alexander; Issue Notification for U.S. Appl. No. 14/064,345, filed Oct. 28, 2013, dated Feb. 24, 2016, 1 pg.

Bally, Alexander; Notice of Allowance for U.S. Appl. No. 14/064,345, filed Oct. 28, 2013, dated Mar. 25, 2016, 10 pgs.

Bally, Alexander; Final Office Action for U.S. Appl. No. 14/686,439, filed Apr. 14, 2015, dated Mar. 31, 2016, 14 pgs.

Bally, Alexander; U.S. Patent Application entitled: Sacrificial Mechanical Link having U.S. Appl. No. 15/049,466, filed Feb. 22, 2016, 56 pgs.

Bally, Alexander; U.S Patent Application entitled: Transfer System With Sacrificial Mechanical Link having U.S. Appl. No. 15/049,477, filed Feb. 22, 2016, 57 pgs.

Bally, Alexander; Issue Notification for U.S. Appl. No. 14/686,439, filed Apr. 14, 2015, dated Dec. 8, 2016, 1 pg.

Bally, Alexander; Non-Final Office Action for U.S. Appl. No. 15/347,070, filed Nov. 9, 2016, dated Jan. 12, 2017; 17 pgs.

Bally, Alexander; Notice of Allowance for U.S. Appl. No. 14/686,439, filed Apr. 14, 2015, dated Aug. 15, 2016, 12 pgs.

Bally, Alex; First Examination Report for Australia Serial No. 2013404103, filed Oct. 28, 2013, dated Jun. 9, 2017, 3 pages.

Bally, Alex; Extended European Search Report for serial No. 13896274.1, filed Oct. 28, 2013, dated Apr. 24, 2017, 6 pgs.

Bally, Alexander; International Search Report and Written Opinion for PCT Application No. PCT/US17/18300, filed Feb. 17, 2017, dated Jun. 26, 2017, 14 pgs.

Bally, Alexander; Invitation to Pay Additional Fees for PCT Application No. PCT/US17/18300, filed Feb. 17, 2017, dated May 3, 2017, 3 pgs.

Bally, Alexander; Notice of Allowance for U.S. Appl. No. 15/347,070, filed Nov. 9, 2016, dated Jul. 27, 2017, 17 pgs.

* cited by examiner

FIG. 6 ic # SECURE EQUIPMENT TRANSFER SYSTEM

REFERENCE TO RELATED APPLICATIONS

This application is a continuation of U.S. patent application Ser. No. 14/064,345, filed Oct. 28, 2013, which is a continuation-in-part of U.S. patent application Ser. No. 13/104,531, filed May 10, 2011, which issued into U.S. Pat. No. 8,579,244 on Nov. 12, 2013, which claims the benefit of U.S. Provisional Application No. 61/332,918, filed May 10, 2010, each of which are hereby specifically incorporated by reference herein in their entireties.

TECHNICAL FIELD

The present invention relates generally to medical equipment transfer systems. More specifically, the present invention relates to a transfer system for reliably, safely and securely transferring life support apparatus between various support platforms when transporting critically ill patients.

BACKGROUND

In the daily care of critically ill patients, a great diversity of medical equipment, including infusion management equipment and supplies, pressure transducers, physiological monitors and other equipment is employed. Such equipment typically is set up at the patient's bedside where it is supported by various stands, racks or hangers. For example, the equipment may be supported by 5-star floor stands, attached to headwalls, suspended from booms that are affixed to the ceiling, floor or wall mounted columns, or on other stationary or mobile platforms.

The difficulty arises when, at times, these patients must be transported from their rooms for administering of various hospital services such as surgery, imaging, radiology or special procedures. Similarly, these patients may need to be transported to other specialized facilities. Such transports are often necessary under emergency conditions while patients are distressed and frail, requiring that such transports be competed rapidly and with minimal disruption of therapy, life support and monitoring.

In the known methods for moving patients in tandem with their support equipment, the caregivers in addition to moving the patient bed must also wheel several intravenous-fluid (IV) stands next to or behind a bed, or pile the equipment onto the mattress next to the patient. These techniques typically prove hazardous because the IV stands may fall and tear out patient connections. Such patient transports are also inefficient and costly because much staff time is required to prepare a patient for transport and many caregivers are needed for moving the equipment in tandem with the bed along corridors, into elevators and through doors.

In an attempt to overcome these shortcomings, several approaches for safer, more efficient and faster transport of patients and life support equipment have been provided in the prior art for the consolidation of life support equipment in a single equipment support structure, wherein the equipment support structure is moved from a support within the room to a mobile support platform such as a patient bed. One known method involves vertically lifting an equipment support structure out of a docking cradle of a headwall or other structure by utilizing the elevating mechanism of the hospital bed and, after transport, depositing the equipment support structure in a stationary docking cradle, again relying on the height adjustment mechanism of the bed.

U.S. Pat. No. 4,945,592 (Sims) teaches use of the hospital bed as a lifting mechanism but fails to provide a safety system to lock the support structure to either the mobile or stationary platform. Further the support equipment cannot be placed on the bed in an optimal position for patient care during transport. Also, conditions on the ground are such that it is difficult to align mobile and stationary platforms for seamless transfers. A further problem in this system is that the system components are not standardized and are therefore costly, and components generally do not conform to effective infection control requirements.

Similarly, U.S. Pat. No. 7,065,812 (Newkirk) also fails to provide a safety system to prevent accidental dislodging of the equipment support structure from engagement to stationary or mobile platforms. Arms and docking mechanisms are not standardized and therefore are costly to manufacture, and the support equipment cannot be moved into an optimal location for effective patient care during transport, nor do components generally conform to effective infection control requirements.

US Published Application No. 2006/0242763 (Graham) fails to provide a safety system to prevent accidental dislodging of the equipment support structure from engagement to stationary or mobile platforms. Additionally, the docking elements are arranged vertically above each other in co-axial relationship, which restricts optimal positioning during transport, fails to provide effective articulation between equipment support structure and patient bed, and therefore does not allow optimal in-transport equipment positioning.

U.S. Pat. Nos. 5,527,125 and 5,306,109 (Kreuzer) provide a safety system to prevent accidental dislodging of the equipment support structure from engagement to stationary or mobile platforms but positions the engagement cones in side-by-side, coplanar relationship which does not permit placement of support equipment vis-a-vis the patient for optimal care during transport. The approach is complex and costly as there is no standardization of crucial docking components, and the safety system relies on a complex and costly sliding mechanism.

U.S. Pat. No. 7,661,641 (Wong) teaches a safety system to prevent accidental dislodging of the equipment support structure from engagement to stationary or mobile platforms but also arranges the docking elements vertically above each other in co-axial relationship which restricts optimal positioning during transport, fails to provide effective articulation between equipment support structure and patient bed and therefore does not allow optimal in-transport equipment positioning. The safety system and the requirement for a mobile base make this approach complex and costly to implement.

Other approaches as disclosed in U.S. Pat. Nos. 7,314,200 and 4,511,158 utilize transfer and docking by connecting to mobile and stationary platforms using a horizontal docking movement rather than a vertical one. These approaches are overly sensitive to misalignment in height and axial orientation of the components to be docked.

In view of the shortcomings of known medical equipment transfer systems, the present invention provides a novel transfer apparatus for transferring said life support equipment between different platforms such as a stationary wall or ceiling support structure and a mobile support platform such as a patient bed. There is therefore a need for a system for transferring patient support equipment from stationary to mobile platforms that is of low mechanical complexity, and that utilizes fewer, standardized, simpler components to permit low-cost manufacturing and reduced service and warranty costs by minimizing field maintenance and extending the mean time between failures. There is also a need for a patient transfer and transport system that assures the life support equipment is securely locked to either the stationary or mobile platform so that it cannot be accidentally removed or dislodged, yet allows seamless transfer of the life support equipment between stationary and mobile platforms that automatically engages the security lock during transfer by utilizing a vertical lift mechanism such as a typical, motorized patient bed. There is a further need for a patient transfer and transport system that minimizes in-service training of caregivers, by making transfer from stationary to mobile platforms intuitive, minimizing training of transport staff by eliminating or automating critical steps in the procedure, and relying less on memory or alertness of personnel. There is still a further need for a patient transfer and transport system that minimizes crevices, exposed fasteners and upward-facing cavities to facilitate effective cleaning and infection control. There is yet a further need for a patient transfer and transport system that is relatively insensitive to the misalignment of equipment typically encountered in hospitals during transfers between stationary and mobile platforms. There is also a need for a patient transfer and transport system that permits nursing staff to position and re-position the support equipment relative to the patient that allows ready access to the patient and facilitates easy monitoring and control of life-support equipment during transport, minimizes the total footprint of the bed and associated equipment, and minimizes the risk of dislodging fluid lines, cables and leads between equipment and patient during transfer between stationary and mobile platforms. Finally, there is a need for a patient transfer and transport system that is articulated to allow caregivers full freedom in repositioning the patient support equipment around the patient's head and allows the articulations to be locked in place during transport.

SUMMARY

In this regard, the present invention provides an equipment transfer device that is transferrable from one support to another support. The transport device is comprised of a clamshell housing having two substantially identical but mirrored outer shells that are held together by screws. Each housing half further comprises two similar, half-conical recesses, preferably disposed on generally parallel, spaced-apart vertical axes such that, when assembled to form said clam-shell, the two housing halves form circular docking cups that are open to the bottom.

The docking cups are spaced apart horizontally along the central plane of the clamshell housing such that each docking cup can receive a docking cone from below, as further described below. Each docking cone is supported on a structure and is capable of moving in a generally vertical direction into engagement or out of engagement along the axis of their respective docking cups while maintaining horizontal separation to avoid interference and collision with one another. The docking cups may be positioned symmetrically on a horizontal plane, but in alternate embodiments the docking cups are preferably disposed on different horizontal levels, with a vertical separation between the upper and lower docking cups.

Additionally, a support post is rigidly trapped and fastened between the two housing halves, preferably in coaxial relationship with the upper docking cup. The support post protrudes from the upper end of the transfer device as a base to which an equipment support structure is rotatably attached. Support structures of various configurations may be interchangeably attached according to specific caregiver requirements.

In accordance with another aspect of the preferred embodiment of the present invention, there is provided a security mechanism that secures a first docking cone, upon engagement to the transfer device, to a first docking cup. The security mechanism only releases the first docking cone from the first docking cup upon insertion and full engagement of a second docking cone in the second docking cup. The security mechanism of this invention prevents accidental disengagement of the transfer device from either the stationary or mobile platforms to which it is docked as it securely locks an engaged docking cone to its respective docking cup. The transfer device may only be disengaged from a first docking cone when another docking cone is fully inserted and engaged in the other docking cup, or vice-versa. The security mechanism operates autonomously without human intervention. It is activated by user control of the vertical movement of the docking activation mechanism, such as the height adjustment of a hospital bed.

It is therefore an object of the present invention to provide a system for transferring patient support equipment from stationary to mobile platforms that is of low mechanical complexity, and that utilizes fewer, standardized, simpler components to permit low-cost manufacturing and reduced service and warranty costs by minimizing field maintenance and extending the mean time between failures. It is a further object of the present invention to provide a patient transfer and transport system that assures the life support equipment is securely locked to either the stationary or mobile platform so that it cannot be accidentally removed or dislodged, yet allows seamless transfer of the life support equipment between stationary and mobile platforms that automatically engages the security lock during transfer by utilizing a vertical lift mechanism such as a typical, motorized patient bed. It is still a further object of the present invention to provide a patient transfer and transport system that minimizes in-service training of caregivers, by making transfer from stationary to mobile platforms intuitive, minimizing training of transport staff by eliminating or automating critical steps in the procedure, and relying less on memory or alertness of personnel. It is yet a further object of the present invention to provide a patient transfer and transport system that minimizes crevices, exposed fasteners and upward-facing cavities to facilitate effective cleaning and infection control. It is a further object of the present invention to provide a patient transfer and transport system that is relatively insensitive to the misalignment of equipment typically encountered in hospitals during transfers between stationary and mobile platforms. It is still a further object of the present invention to provide a patient transfer and transport system that permits nursing staff to position and re-position the support equipment relative to the patient that allows ready access to the patient and facilitates easy monitoring and control of life-support equipment during transport, minimizes the total footprint of the bed and associated equipment, and minimizes the risk of dislodging fluid lines, cables and leads between equipment and patient during transfer between stationary and mobile platforms. Finally, it is an object of the present invention to provide a patient transfer and transport system that is articulated to allow caregivers full freedom in repositioning the patient support equipment around the patient's head and allows the articulations to be locked in place during transport.

Also disclosed is a method of using a transfer system, the method comprising: supporting a first docking cone of the transfer system by a first support platform to orient a docking cone axis of the first docking cone with a vertical axis; inserting the first docking cone into a first docking cup of a transfer device of the transfer system; and locking the first docking cone within the first docking cup by a security mechanism of the transfer device, the security mechanism comprising a first security lever and a second security lever.

Also disclosed is a method of using a transfer system, the method comprising: supporting a first docking cone of the transfer system by a first support platform to orient a docking cone axis of the first docking cone with a vertical axis; locking the first docking cone within a first docking cup of a transfer device of the transfer system by a security mechanism of the transfer device, the security mechanism and a tip of the first docking cone housed within the transfer device; supporting a second docking cone of the transfer system by a second support platform; engaging the second docking cone within a second docking cup of the transfer device, a tip of the second docking cone housed within the transfer device; and unlocking the first docking cone from the transfer device when the second docking cup is fully received within the second docking cup.

These together with other objects of the invention, along with various features of novelty that characterize the invention, are pointed out with particularity in the further description annexed hereto and forming a part of this disclosure. For a better understanding of the invention, its operating advantages and the specific objects attained by its uses, reference should be had to the accompanying drawings and descriptive matter in which there is illustrated a preferred embodiment of the invention.

BRIEF DESCRIPTION OF THE DRAWINGS

In the drawings which illustrate the best mode presently contemplated for carrying out the present invention:

FIG. 6 is a side view of the transfer system docked to a mobile support platform and the mobile support platform raised to undock the transfer device from the stationary platform during transfer;

DETAILED DESCRIPTION

Figure 1:
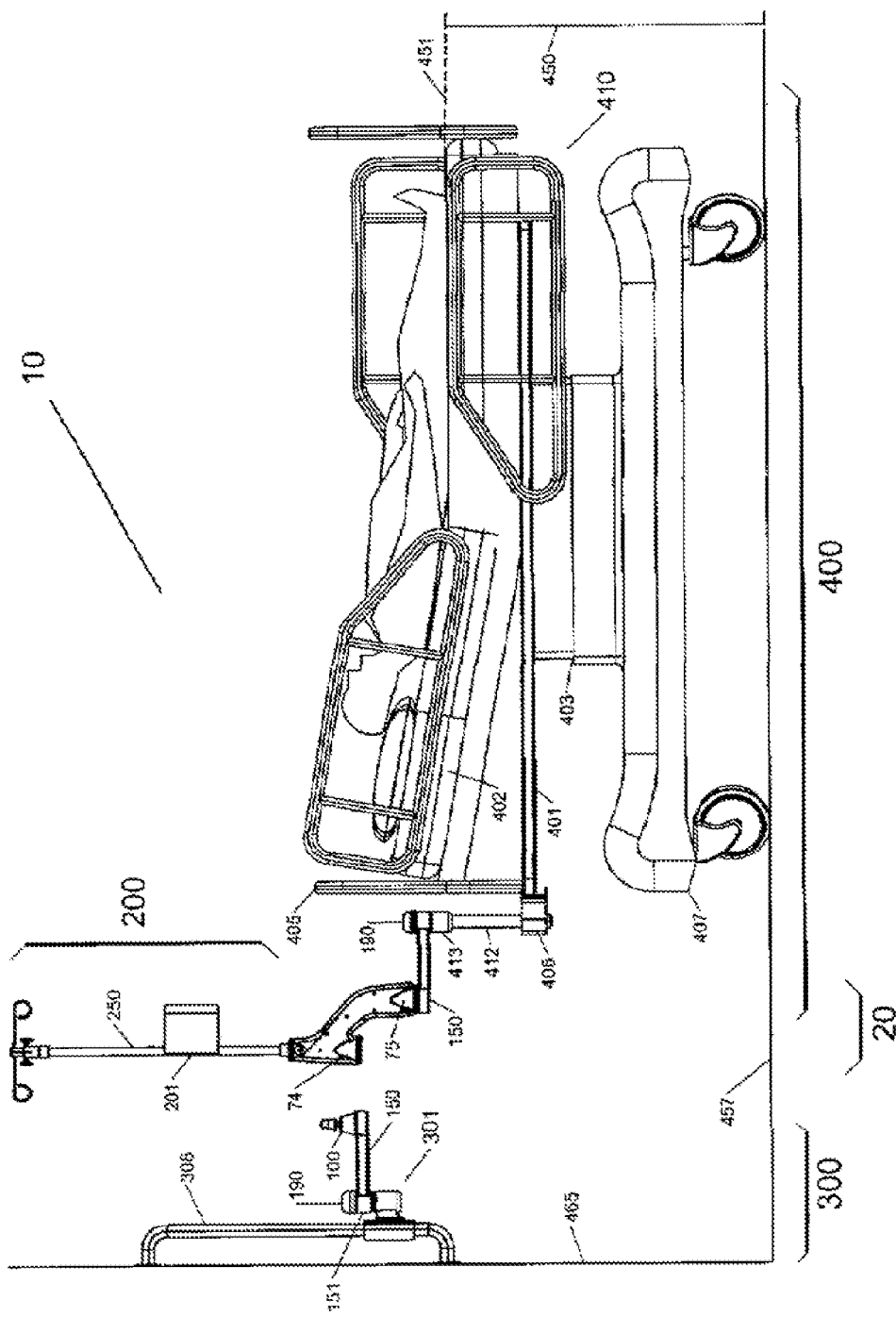
FIG. 1 is a side view of the transfer system of the present invention docked to a mobile support platform in preparation for transfer.

Now referring to the drawings, the equipment transfer system is shown and generally illustrated in the figures. As can be seen the principal component of the transfer system is a transfer device 20 that can be selectively supported and moved between a stationary support platform 300 and a mobile support platform 400 to facilitate the transfer of patient care apparatus 200 supported thereon.

Turning to FIG. 1, the transfer system 10 includes a stationary support platform 300, a mobile support platform 400 and a transfer device 20 that supports a patient care apparatus 200 and is capable of transferring the patient care apparatus 200 between a stationary support platform 300 and a mobile support platform 400 and vice-a-versa. Within the scope of the present invention the term "transfer" refers to transferring patient support equipment between stationary support platforms including walls, headwalls, ceiling-mounted or wall-mounted booms from various manufacturers, free-standing and/or movable columns and other structures typically found in hospital rooms and treatment facilities to which a stationary cone arm connector 301 may be attached, and mobile support platforms such as patient beds, gurneys, wheelchairs, ambulances, helicopters or other mobile platforms, and vice-versa. As anyone familiar with the art will appreciate, substituting alternative rotatable attachment means, alternative stationary support platforms, alternatives to post 308 and/or stationary cone arm connectors 301, as well as transfers between stationary platforms or between mobile platforms, are within the scope of this invention.

Figure 2:
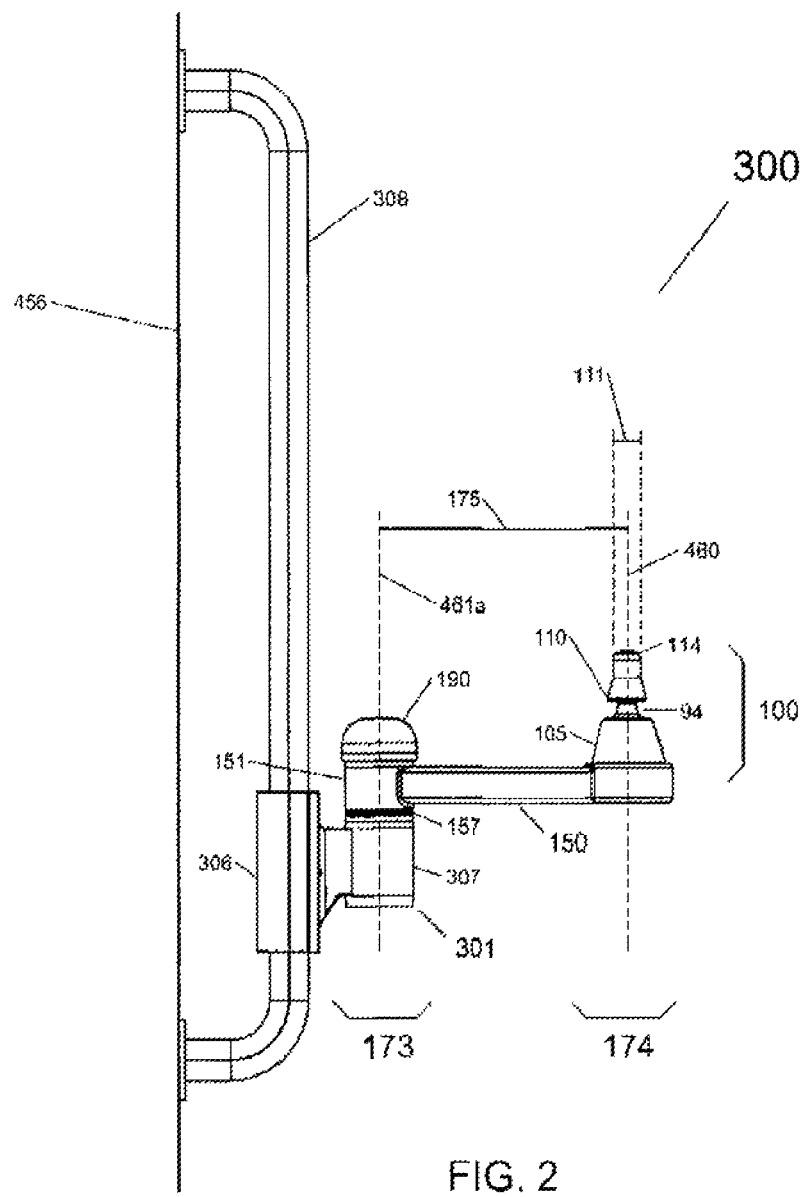
FIG. 2 is a side view of a stationary support platform attached to a wall.
Figure 3:
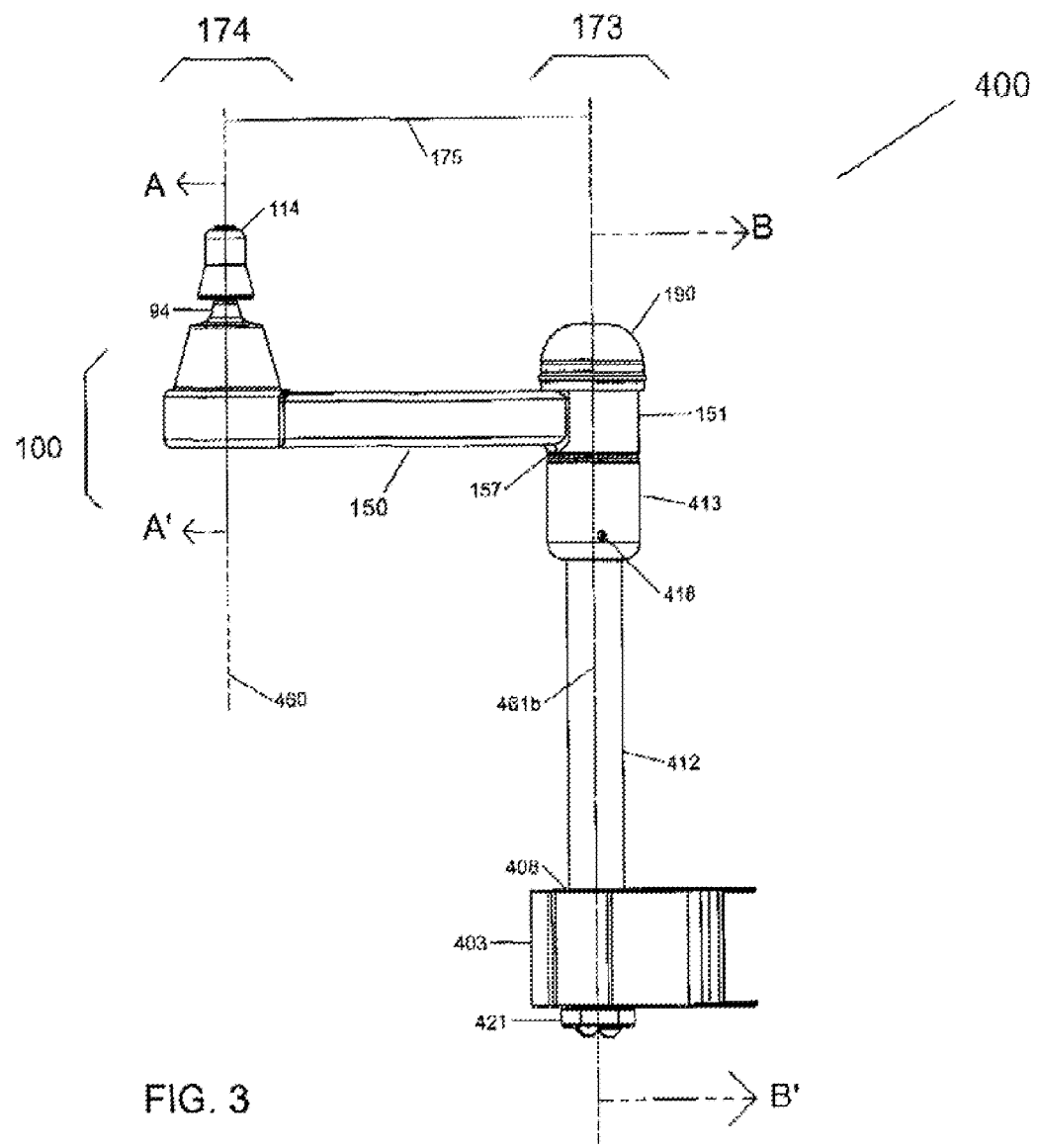
FIG. 3 is a side view of a mobile support platform showing an attachment bracket.

Referring to stationary support platform 300 and mobile support platform 400 of the preferred embodiment, as shown in FIGS. 1-3, platforms 300 and 400 may both support a cone arm 150. Cone arm 150 has a distal end 174 and a proximal end 173. The distal end 174 comprises docking cone 100 for docking with transfer device 20 and the proximal end 173 comprises arm joint 151 which may be attached to stationary or mobile support platforms 300 or 400, respectively. Cone arm 150 may be attached to a stationary support platform, such as post 308, or directly to a wall 465 using stationary cone arm connector 301. Cone arm 150 may also be attached to a mobile support platform 400, such as a hospital bed, as more fully described below, using mobile cone arm adapter 413 which is mated to accessory bracket 406 of a hospital bed 410 by means of bed post 412 or other known connection.

Figure 4:
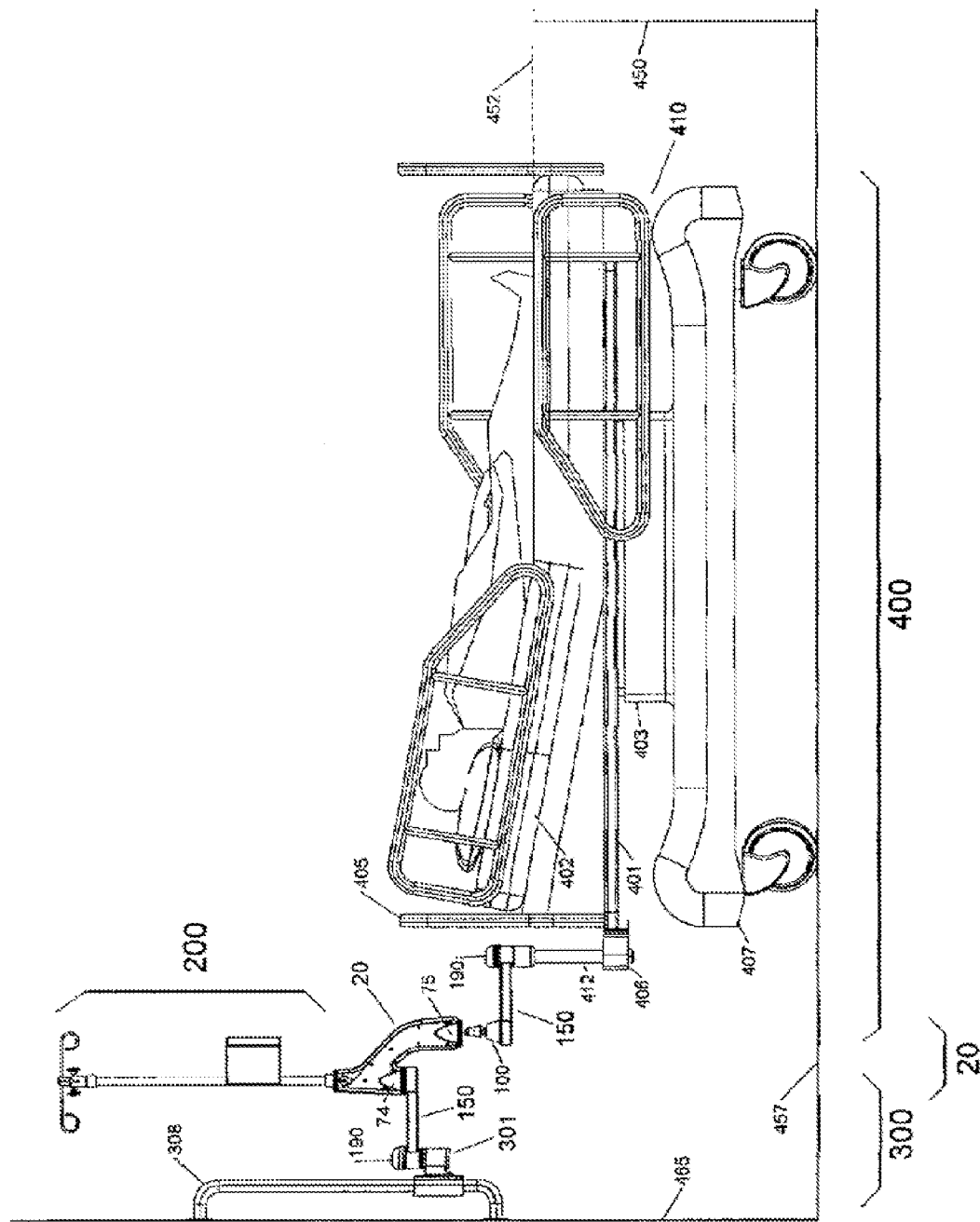
FIG. 4 is a side view the transfer system docked to a stationary support platform with the mobile support platform lowered for docking to the transfer device in preparation for transfer.
Figure 9:
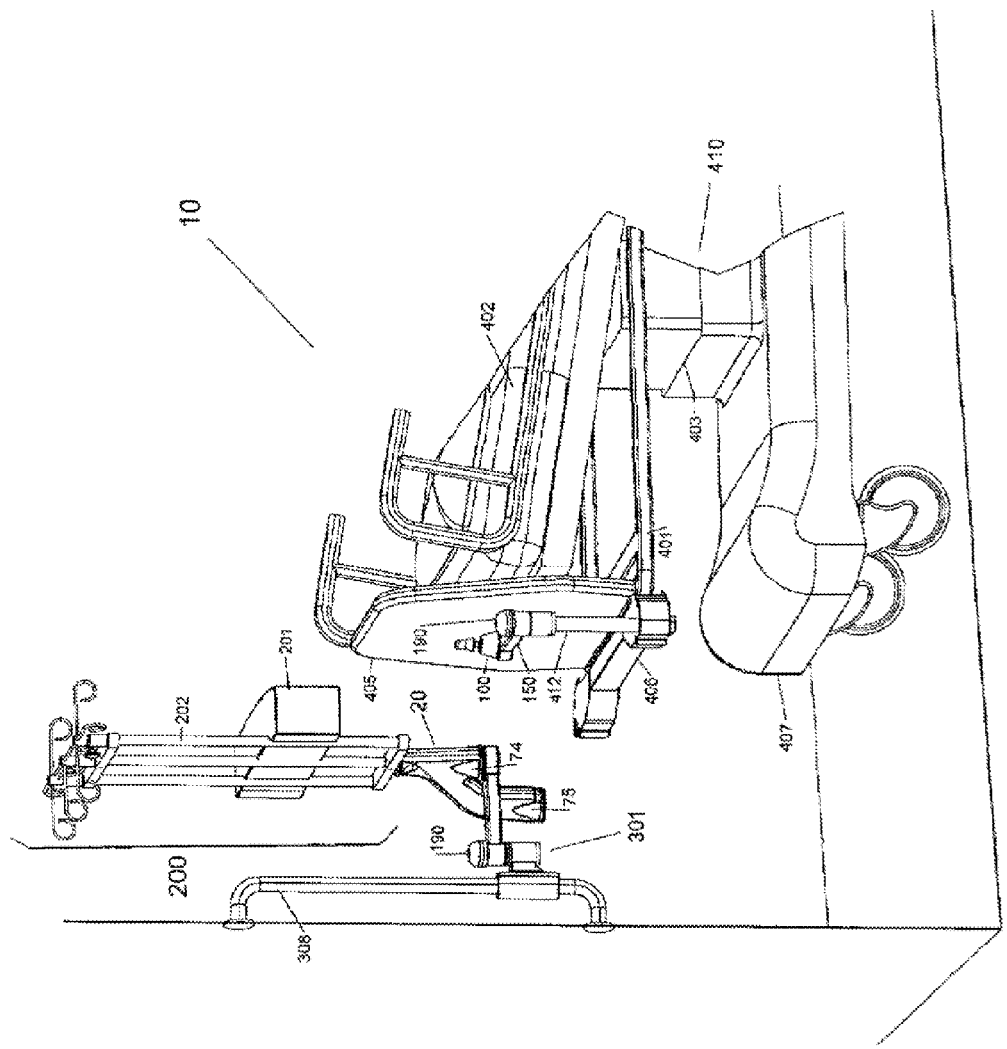
FIG. 9 is a perspective view of the transfer system with a transfer device docked to a stationary support platform and with the docking arm of the mobile support platform and the transfer device on the stationary support platform stowed after transport, and the mobile support platform partially cut away.

As shown in FIGS. 4 & 9, when treated in a hospital room, a patient typically may be attached to patient care apparatus 201 connected to an equipment support structure 200. The equipment support structure preferably is attached to transfer device 20 and rotatably docked to docking cone 100 of a cone arm 150 that is rotatably joined to a stationary cone arm connector 301. Cone arm 150, docking cone 100 and cone arm connector 301 provide articulation so that stationary support platform 300 may be positioned for optimal patient care. Having patient care apparatus 201 physically detached from hospital bed 410, while a patient is in a room, is preferred in many health care facilities in order to provide unobstructed patient access all around hospital bed 410. As used herein, the term "docking" and "docking maneuver" refers to inserting a docking cone into a docking cup generally in coaxial alignment and in a load-bearing relationship where cone arm 150 supports transfer device 20 and patient care apparatus 201.

Figure 16:
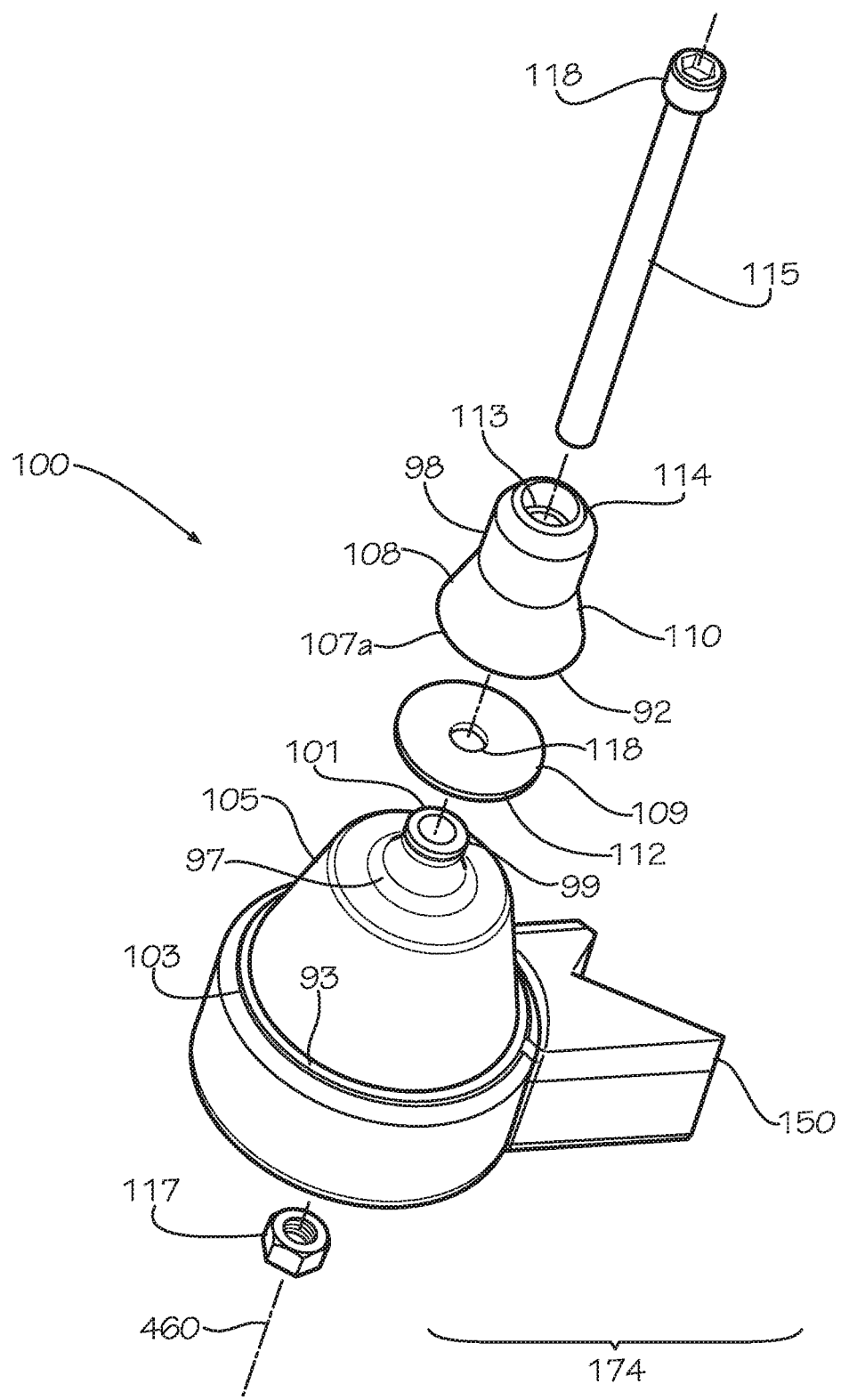
FIG. 16 is an exploded view of a docking cone.

As shown in FIGS. 2 and 3, the cone arms 150 that are attached to both the stationary support platform 300 and the mobile support platform 400 are substantially identical. In the preferred embodiment, arm length 175 is approximately 9.5 inches. However, arm length 175 may reasonably range between 4 inches and 15 inches, although shorter and longer arm lengths 175 may be used to meet specific requirements, and cone arms 150 of different lengths may be employed in a single transfer system 10. In addition, in the preferred embodiment shown in FIGS. 14 & 16, arm joint 151 and docking cone 40, as well as the components required in the arm joint 151 for achieving joint stability and user adjustment, have both been standardized in order to minimize manufacturing cost and parts inventory. As anyone familiar with the art may recognize, one or more additional articulating arm segments may be installed between arm joint 151 and stationary arm connector 301, and/or between mobile cone arm adapter and arm joint 151, in order to extend the reach and flexibility of system 10.

Figure 12:
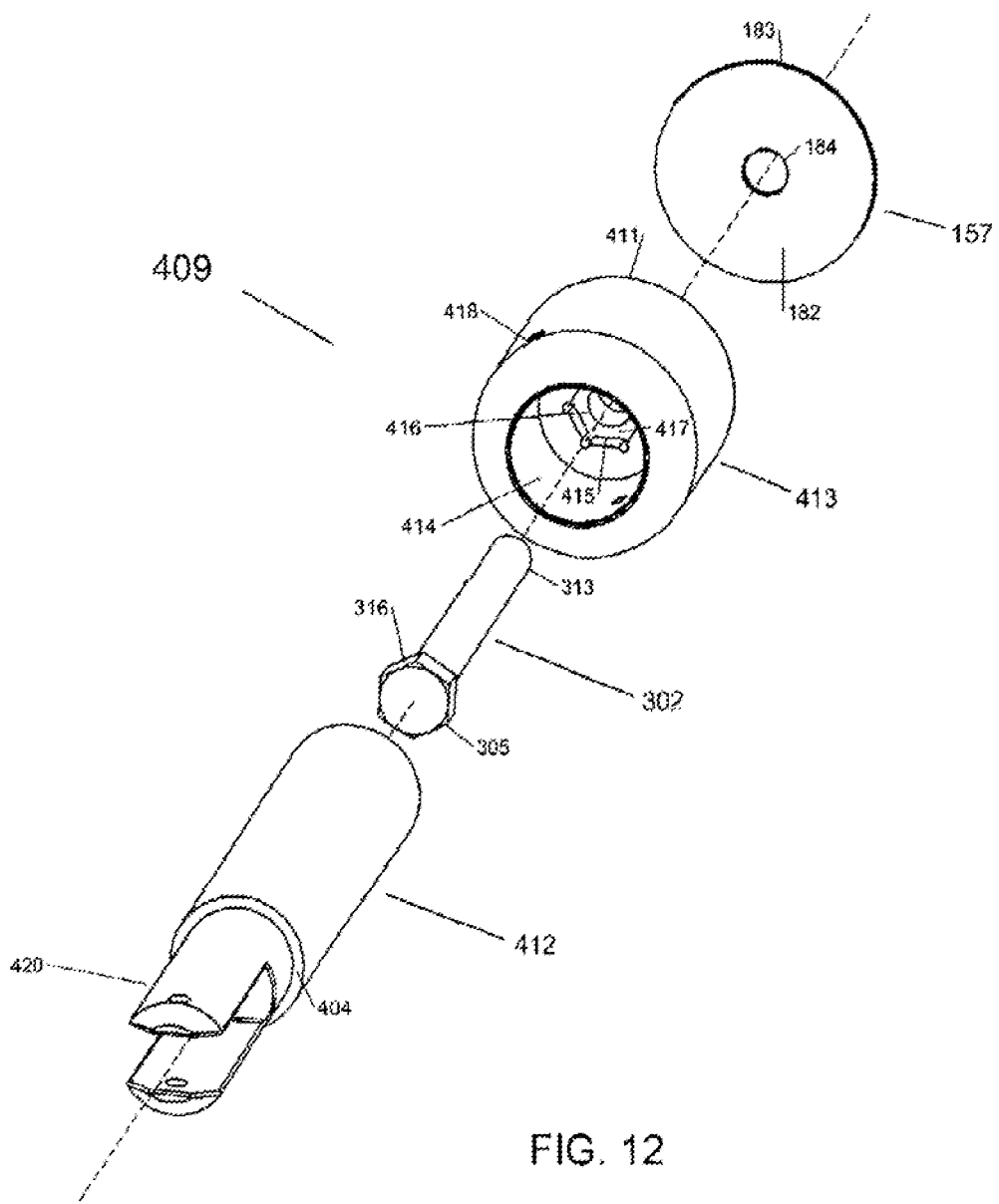
FIG. 12 is an exploded view of a bed connection.
Figure 13:
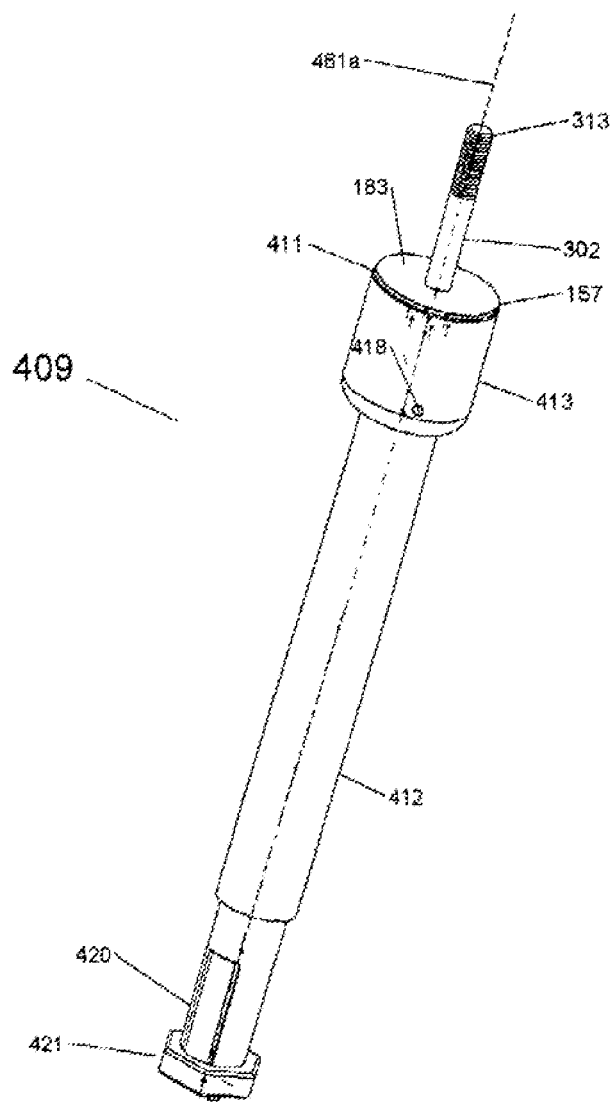
FIG. 13 is a perspective view of a bed connection.
Figure 14:
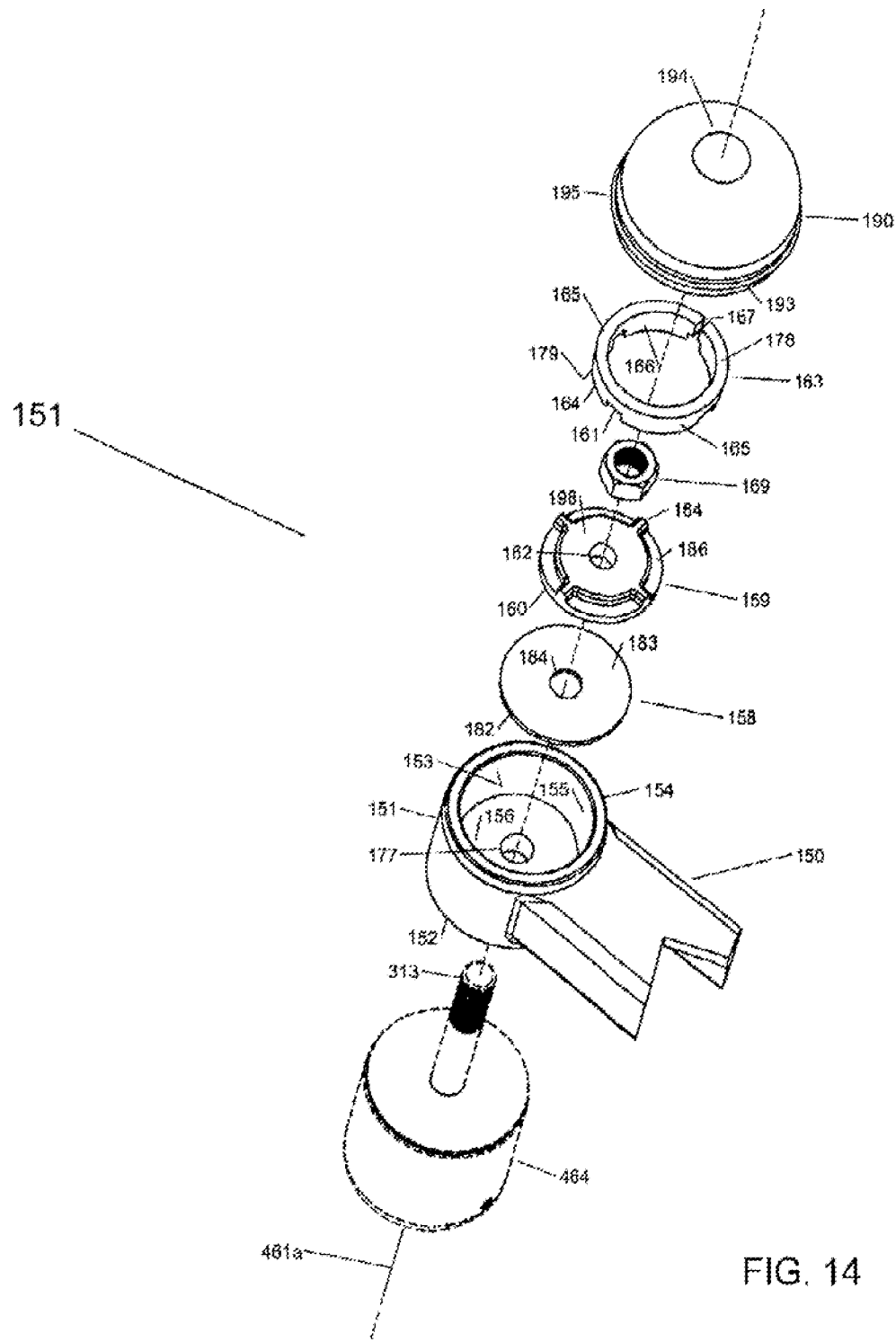
FIG. 14 is an exploded view of an arm joint showing attachment to either a stationary cone arm connection or a bed connection represented by a dotted outline.
Figure 15:
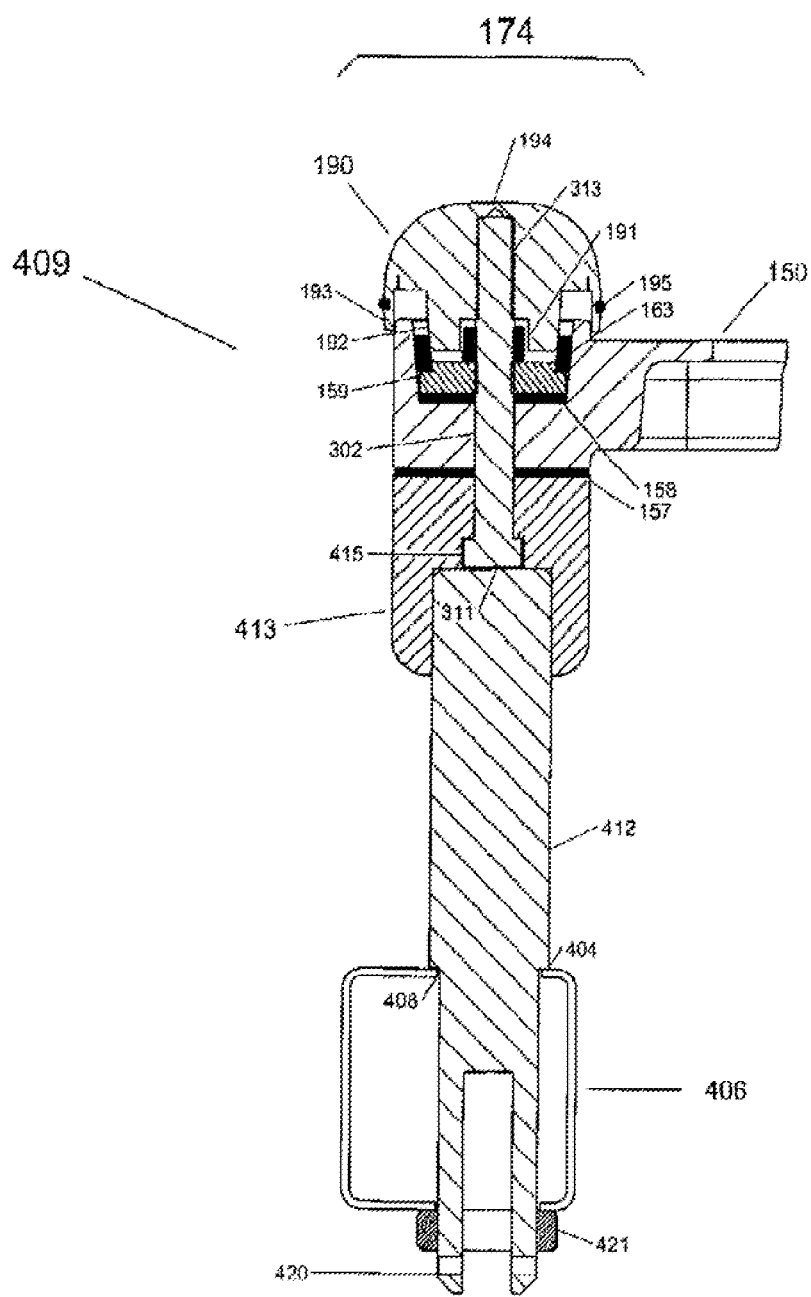
FIG. 15 is a sectional side view of a bed connection taken along line B-B' of FIG. 3.

As shown in FIGS. 10-13, stationary arm connector 307 and mobile cone arm adapter 413 have a stationary contact interface 312 and a mobile contact interface 411, respectively. Both contact interfaces 312, 411 are substantially identical and enable essentially identical attachment to arm joint 151 located at the proximal end 173 of cone arm 150, regardless whether attached to mobile or stationary platforms. As shown in FIGS. 14 & 15, standardization of attachment and joint tensioning components of cone arms 150 is instrumental in reducing the complexity and manufacturing cost of transfer system 10. Stationary contact interface 313 is a flat surface 312 and is perpendicular to the longitudinal axis of bolt 302. Bolt 302 protrudes from stationary contact interface 312 and is held in place and secured against rotation by capturing hexagonal bolt head 305 with bolt head restraints 310. Analogously, the mobile contact interface is perpendicular to longitudinal axis of bolt 302. Bolt 302 protrudes from mobile contact interface 411 and is held in place and secured against rotation by capturing hexagonal bolt head 305 with bolt head restraints 310.

Figure 10:
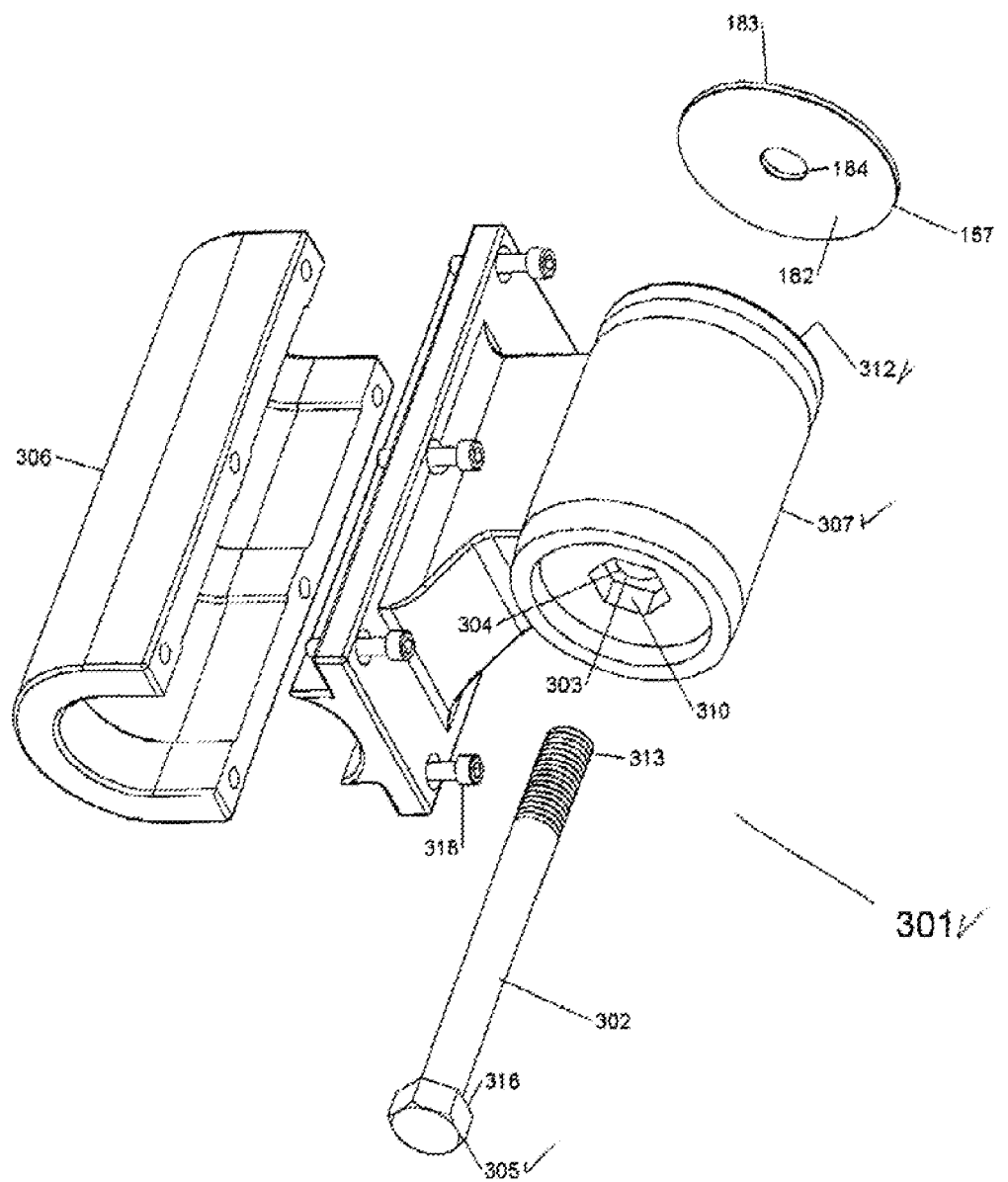
FIG. 10 is an exploded view of a stationary cone arm connector.

As shown in FIGS. 2, 9 & 10, stationary cone arm connector 301 is comprised of arm connector 307 and clamp 306. Arm connector 307 and clamp 306 cooperate, in a clamping and load-bearing relationship, to firmly attach stationary cone arm connector 301 to post 308 by means of attachment screws 318.

In order to achieve low manufacturing cost, the number of parts and components required in transfer system 10 is minimized by standardization. Cone arm 150 used with a stationary support platform 300 is preferably substantially identical to cone arm 150 used with a mobile support platform 400, and the components required and method used for attaching cone arm 150 to arm connector 307 of stationary support platform 300, as shown in FIG. 2, is preferably substantially identical to the components required and method used for attaching cone arm 150 to mobile cone arm adapter 413 of mobile support platform 400, as shown in FIG. 3.

Figure 11:
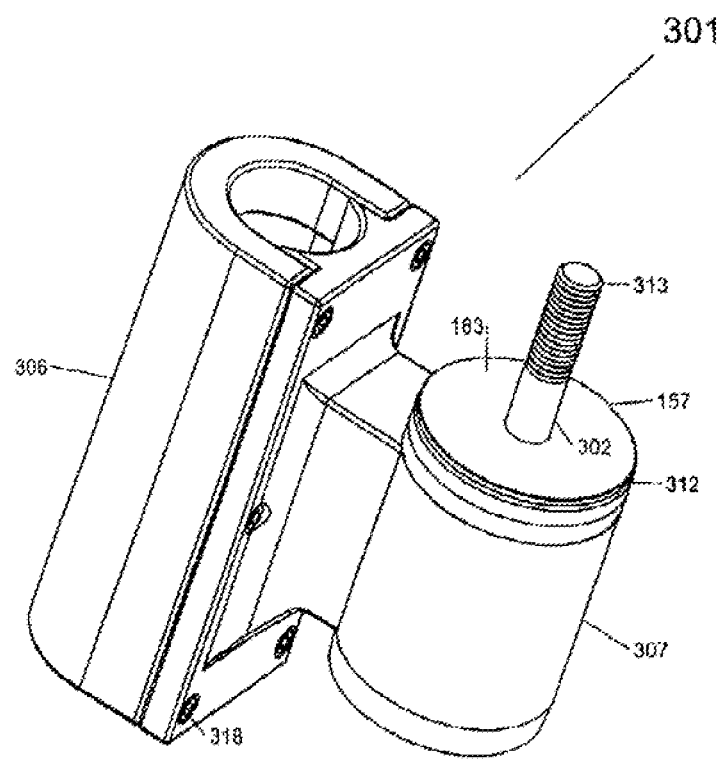
FIG. 11 is a perspective view of a stationary cone arm connector.

As shown in FIGS. 2, 11 & 12, arm joint 151 may be attached to stationary arm connector 307 to form a rotatable joint that permits cone arm 150 to rotate on arm connector axis 461*a* in a horizontal plane. The treaded bolt end 313 of bolt 302 is pushed up through bolt hole 315 with the bolt head base 316 of hexagonal head 305 in contact with bolt head bearing surface 303 and hexagonal head 305 in engagement with bolt restraints 310 to prevent rotation of bolt 302. Threaded bolt end 313 may issue from the center of, and perpendicularly to, stationary contact interface 312. Thrust bearing 157 may be placed on stationary contact interface 312 in coaxial relationship with bolt 302 and with lower bearing face 182 in coplanar and sliding relationship with stationary contact interface 312 to constitute a standardized attachment for cone arms 150 to stationary support platforms 300.

As shown in FIGS. 11-15, the connections between cone arm 150 and arm connector 307, and cone arm 150 and mobile cone arm connector 413, are substantially identical. Cone arm 150 may be placed onto bolt 302 with bolt bore 177 in coaxial relationship, and with the upper bearing face 183 of thrust bearing 157 in coplanar and sliding relationship with bearing surface 152 of arm joint 151, and with threaded bolt end 313 extending coaxially up through recess 153 of arm joint 151. Lock thrust bearing 158 may be placed over threaded bolt end 313 with the lower bearing face 182 of lock thrust bearing 158 in coplanar and sliding relationship with inner joint pressure surface 156. Pressure plate 159 may be threaded onto the treaded bolt end 313 by means of tapped center hole 162, with pressure surface 160 in coplanar relationship with, and tightened against, the upper bearing face 183 of lock thrust bearing 158 in order to cause tension on bolt 302 and take up slack in arm joint 151. Jam nut 169 is threaded onto threaded bolt end 313 and tightened against pressure plate 159 in jam-nut relationship to secure pressure plate 159 against rotation relative to bolt 302 during continued use of transfer system 10.

As shown in FIGS. 14 & 15, adjustment knob 190 is in threaded engagement with threaded bolt end 313 of bolt 302 that protrudes through jam nut 169. Clockwise or counterclockwise rotation, respectively, of adjustment knob 190, permits users to adjust the friction between cone arms 150 and stationary and mobile support platforms 300 and 400, respectively, without affecting the load bearing ability or stability of arm joint 151. Adjustment knob 190 has a threaded center boss 191 with tapered outer surface 192, crown 194 and side skirt 193. Side skirt 193 is sized to protrude over, and overlap with, recess rim 154 of cone arm 150 when adjustment knob 190 is fully tightened to facilitate infection control. To offer better hand purchase when users tighten and loosen adjustment knob 190, crown 194 and side skirt 193 may be grooved to retain an external O-ring 195 or may be indented, serrated or otherwise shaped (not shown). Tapered outer surface 192 of threaded center boss 191 cooperates with friction wedge 163 to control joint friction.

Friction wedge 163 is an annulus with essentially parallel upper and lower surfaces 178, 179, respectively, outer wedge taper 165, inner wedge taper 166, and axial expansion cut 167 that permits friction wedge 163 to expand in response to tightening of adjustment knob 190. Lower wedge surface 179 is in contact with base surfaces 186 of registration recesses 161. Registration recesses 161 are sized to interdigitate with matching registration protrusions 164 on pressure plate 159 to limit rotation of friction wedge 163 relative to pressure plate 159 in order to prevent the known problem of tightening or loosening an arm joint, respectively, when a cone arm is moved clockwise or counterclockwise.

Tightening adjustment knob 190 on bolt 302 pushes friction wedge 163 against pressure plate 159 and forces tapered outer surface 192 of threaded center boss 191 of adjustment knob 190 against inner wedge taper 166 of friction wedge 163 causing friction wedge 163 to expand. Outer wedge taper 165 of friction wedge 163 is forced against inner wall 155 of recess 153 of arm joint 151 to progressively increase or decrease joint friction when a user tightens or loosens adjustment knob 190.

Analogously, cone arm 150 may be attached to mobile support platform 300 by means of mobile cone arm adapter 413 fastened to vertical bed post 412. There are many known mobile support platforms 400, including hospital beds, stretchers and gurneys from various manufacturers, special procedure support devices, wheelchairs, and other structures typically found in hospitals and treatment facilities to which a mobile cone arm adapter 413 may be adapted for attachment to alternative stationary and mobile support platforms 300, 400 to enable system 10 to be used with known variations in known attachment methods. Such adaptations, as anyone familiar with the art may recognize, are within the scope of this invention. Analogously, as shown in FIGS. 3, 13 & 14, arm joint 151 may also be attached to mobile cone arm adapter 413 to form a rotatable joint that permits cone arm 150 to rotate on bed post axis 461b in a horizontal plane. Treaded bolt end 313 of bolt 302 is pushed up through bolt hole 315 with the bolt head base 316 of hexagonal head 305 in contact with bolt head bearing surface 303 and hexagonal sides of bolt head 305 in engagement with bolt restraints 310 to prevent rotation of bolt 302. Threaded bolt end 313 may issue from in the center of, and perpendicularly to, mobile contact interface 411. A thrust bearing 157 may be placed on mobile contact interface 411 in coaxial relationship with bolt 302 and with lower bearing face 182 of thrust bearing 157 in coplanar and sliding relationship with mobile contact interface 411 to constitute a standardized attachment for cone arms 150 to mobile support platforms 400.

As shown in FIGS. 1 & 2-9, transfer device 20 is selectively attachable to the docking cones 100 of cone arms 150 in order to transfer patient care apparatus 201 between stationary support platforms 300 and mobile support platforms 400. The transfer device 20 supports equipment support structure 200 by means of support post 41 that is rigidly attached to, and protrudes out of, upper end 33 of clamshell housing 21 and rotatably engages equipment support structure 200. Hospital staff may attach patient care apparatus 201 to equipment support structure 200, such as infusion management devices and supplies, monitoring equipment, and other life support apparatus that may be required for the care of critically ill patients. The vertical axis of rotation (not shown) of equipment support structure 250 preferably is coaxial with upper docking cone axis 462.

The configuration of equipment support structure 200 may vary depending on type and number of patient care apparatus being used, hospital protocols, type of therapy or life support requirements. However, various configurations of equipment support structures 200 preferably share the capability of being interchangeably attached to support post 41. Generally, transfer device 20 and equipment support structure 200 are rotatably joined and paired for the duration of a patient's hospital stay or longer.

Mobile support platform 400 of the preferred embodiment preferably is a hospital bed 410. In hospital beds, mattress height 450 typically is adjustable between working height 451, low docking level 152 and high docking level 453 by lift mechanism 403 that may be powered by an electric motor, hand crank or other mechanism. FIG. 1 shows mattress 402 of hospital bed 410 at working height 451—a height typically chosen by hospital staff to perform their care giving tasks. Height-adjustable frame 401 may comprise an accessory bracket 406 near headboard 405 of hospital bed 410. Accessory brackets 406 on conventional hospital beds 410 provide for attachment of accessories such as push handles, foldable IV poles, guide wheels or orthopedic frames, and therefore offer a suitable attachment structure for transfer device 20. As shown in FIGS. 1 & 15, cone arm 150 may be attached to accessory bracket 406 of hospital bed 410 by means of the threaded lower end 420 of bed post 412 that may be inserted vertically, in fixed, load-bearing and non-rotating relationship, into one of the accessory connection openings such as accessory sockets 408 available in typical accessory brackets 406, or it may be otherwise attached to the structure of a hospital bed by welds, mechanical fasteners, clamps or other known fastening methods.

The method of preparing a patient for transport, safely transferring patient care apparatus 201 from attachment in the room to attachment to bed 410, safely transporting a patient to another location, and safely and expeditiously returning the patient to a room, as shown in FIGS. 1-5, 11 & 14, is described below. As used in this disclosure, the term "transport" refers to moving a patient in tandem with life support equipment attached to a mobile platform such as a patient bed, gurney, wheelchair, ambulance, helicopter or other mobile platform between locations within or between medical facilities, such as intensive care rooms, operating rooms, radiology and other imaging facilities, catheterization labs, or between buildings and hospitals.

Figure 5:
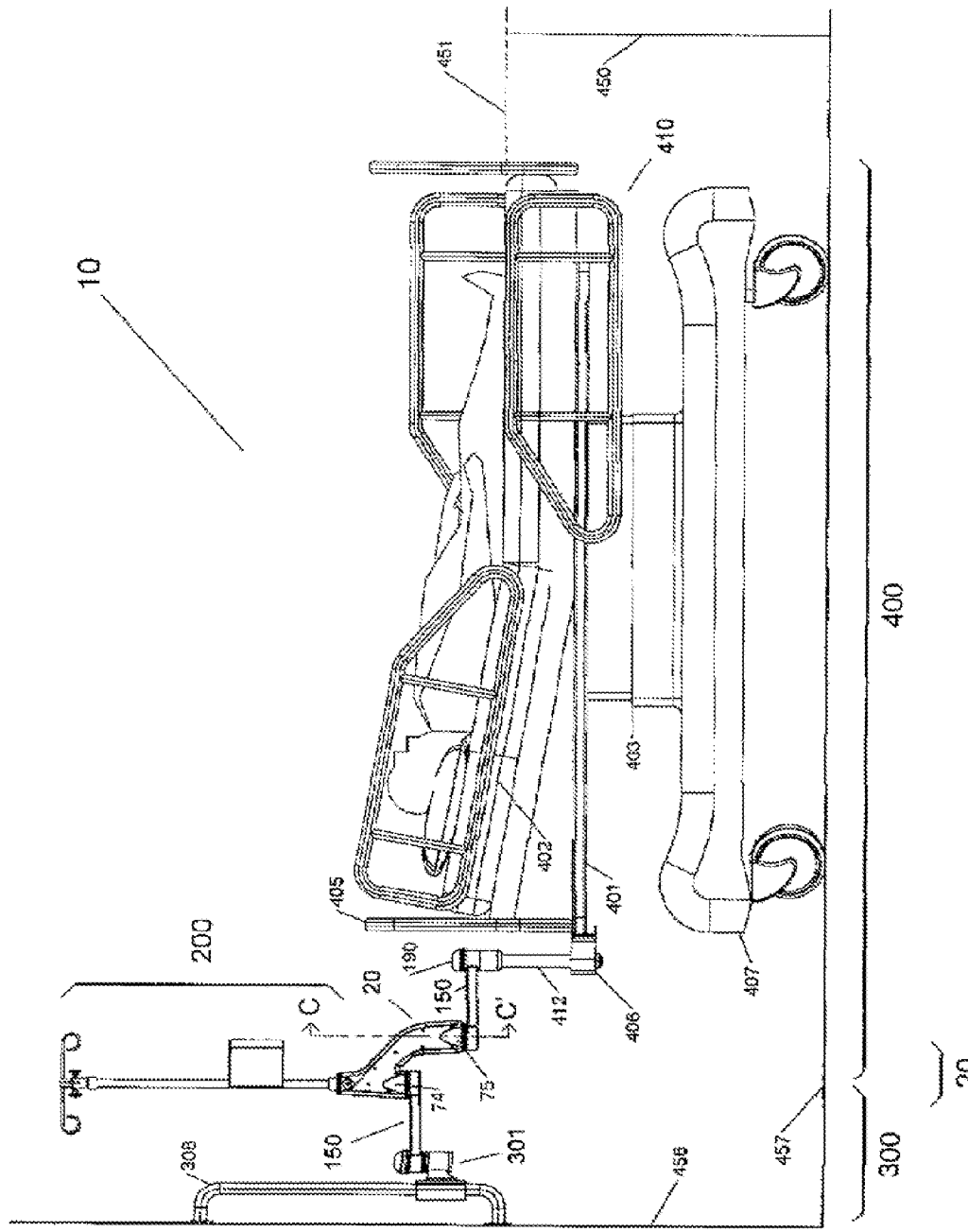
FIG. 5 is a side view of the transfer system docked to both a mobile support platform and the mobile support platform to simultaneously dock the transfer device during transfer.

Before transporting a patient from a room to another location, as shown in FIG. 4, upper docking cup 74 of transfer device 20 typically will be docked with, and secured to, a stationary support structure 300. In preparation of patient transport, transfer device 20 may be repositioned so that the lower docking cup faces hospital bed 410, and hospital bed 410 preferably may be moved closer to the stationary support platform 300. Activation of lift mechanism 403 may lower mattress height 450 from working height 451 to low docking level 452 to permit docking cone 100 of mobile support platform 400 to be maneuvered directly underneath, and into generally coaxial alignment with, lower docking cup 75 of transfer device 20. Activation of lift mechanism 403 of hospital bed 410 may raise mattress 402 and also raise docking cone 100 of mobile support platform 400, causing it to dock with transfer device 20. As shown in FIG. 5, docking cone 100 attached to stationary support platform 300 and docking cone 100 attached to mobile support platform 400 are simultaneously engaged in their respective docking cups 74, 75. Under continued activation of lift mechanism 403, security mechanism 120 automatically releases transfer device 20 from the stationary docking cone 100 and locks transfer device 20 to the mobile docking cone 100, as more fully described below.

Figure 6:
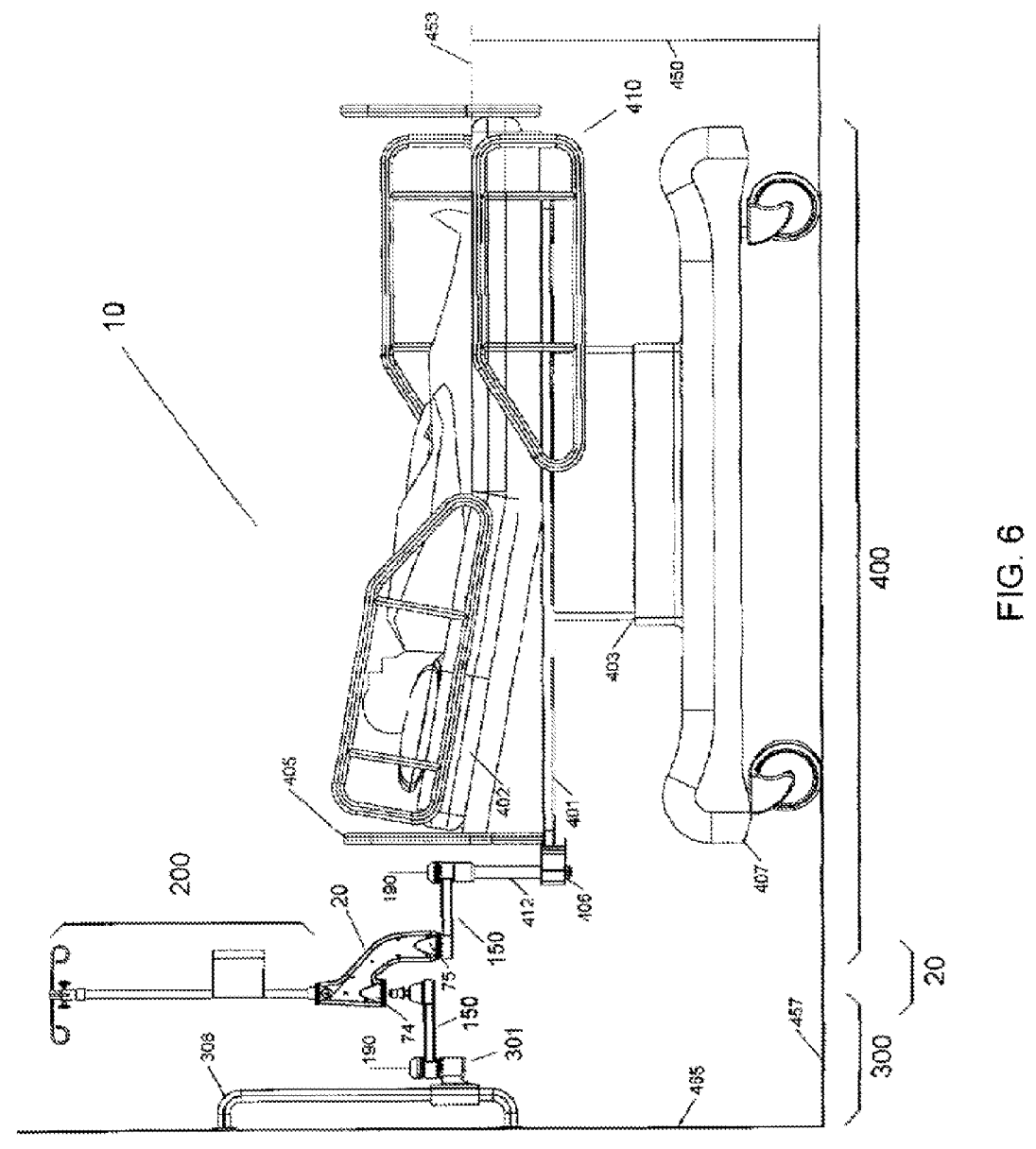

As shown in FIG. 6, continued activation of lift mechanism 403 lifts transfer device 20 out of engagement with stationary docking cone 100 until the transfer device clears the stationary docking cone. In the preferred embodiment, cone arms 150, mobile cone arm adapter 413, stationary cone arm connector 301, adjustment knobs 190, and upper and lower docking cups 74, 75 of transfer device 20 constitute a system of pivoting linkages that permit caregivers to position patient care apparatus 201 where it is needed for optimal patient care, and the arm length 175, as well as the spacing of upper and lower docking cup axes 462 and 463 offer a practical trade-off between easy adjustability and low cost.

Figure 7:
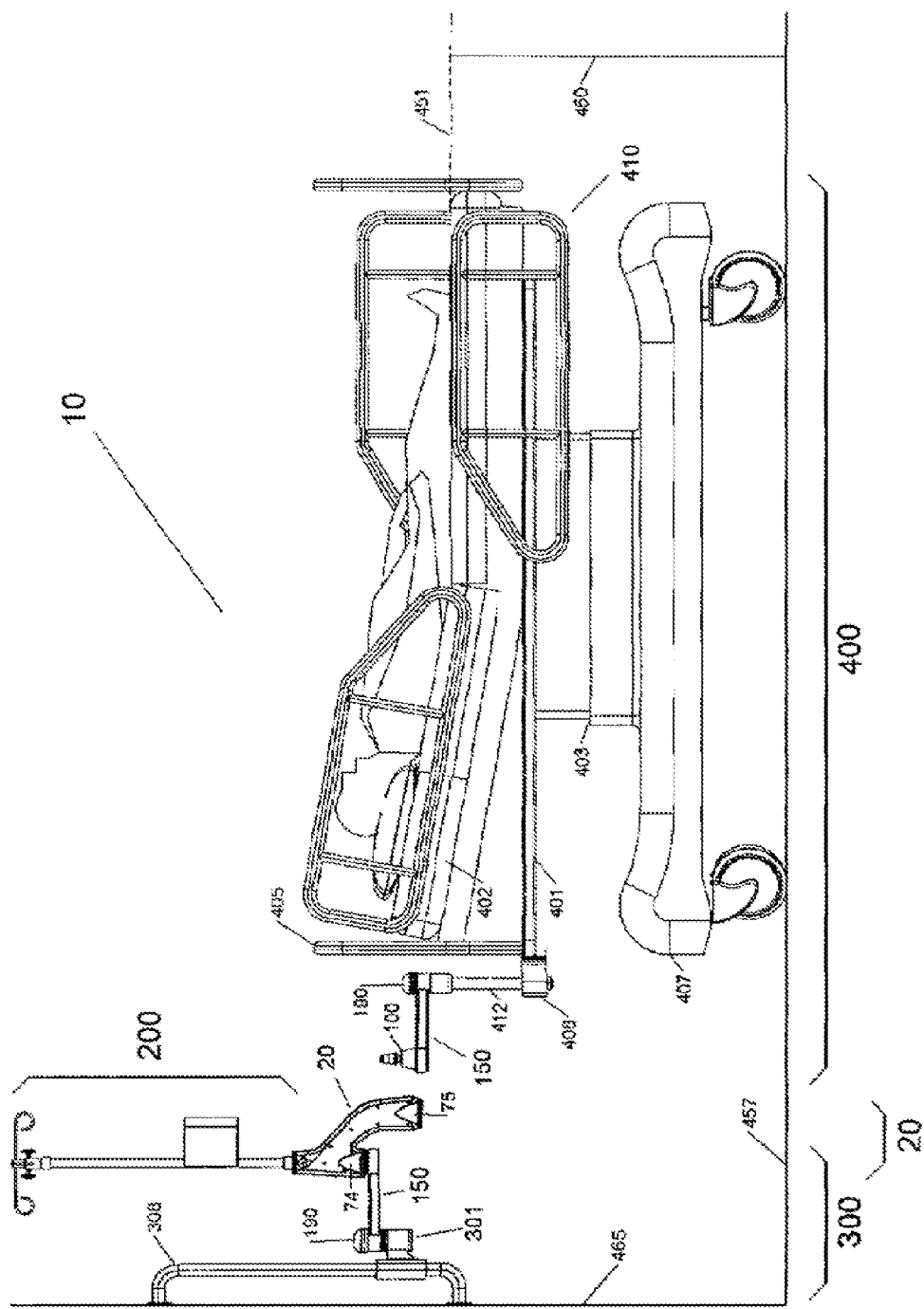
FIG. 7 is a side view of the transfer system docked to a stationery support platform and with the transfer device disengaged from a mobile support platform during transfer.
Figure 8:
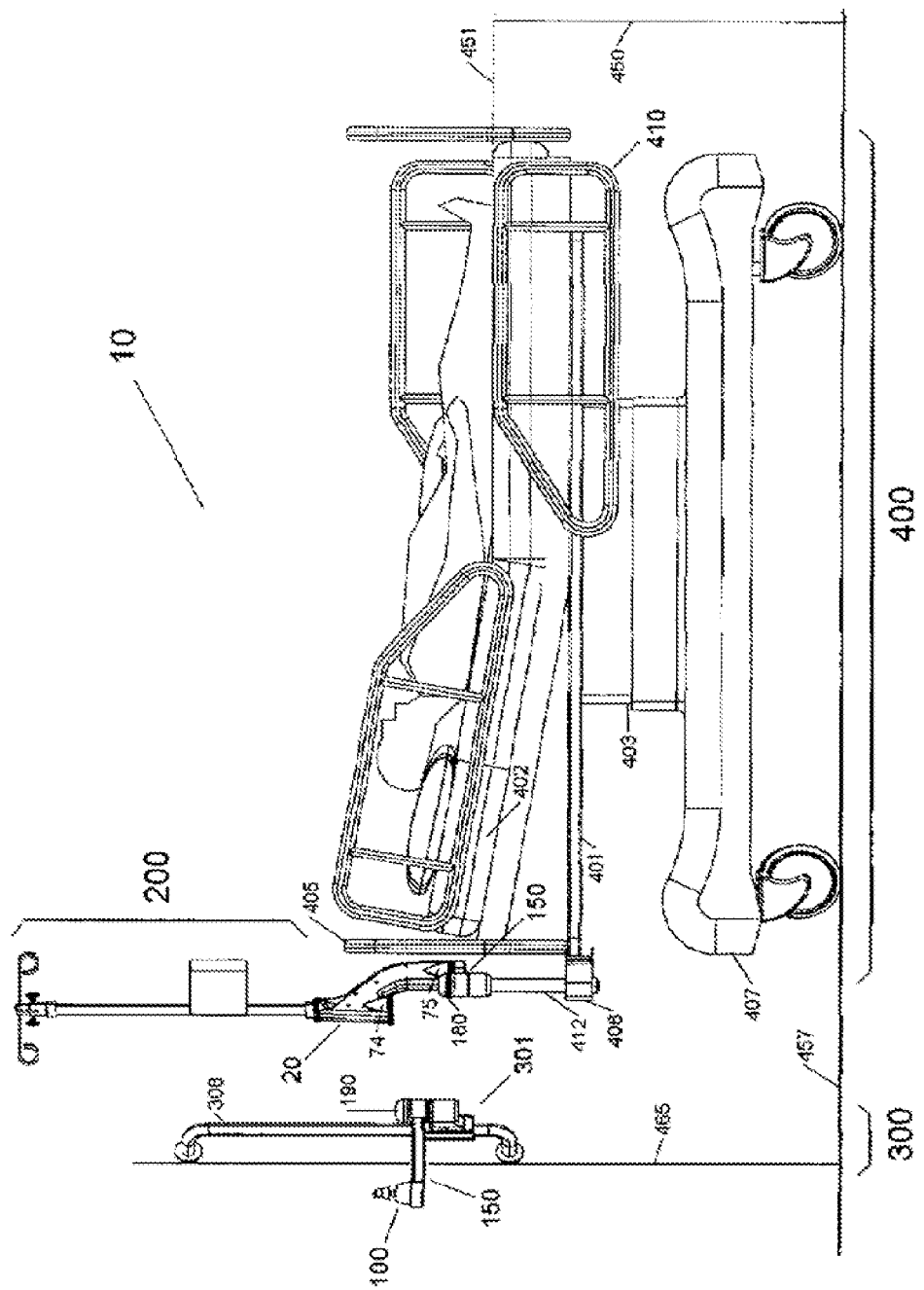
FIG. 8 is a side view of the transfer system docked to a mobile support platform during transfer and the docking arms on the stationary platform and the transfer device on the mobile support platform stowed for transport.

As shown in FIG. 7, moving hospital bed 410 away from stationary support platform 300 and out of docking alignment enables the medical staff to reverse lift mechanism 403 to lower mattress height 450 to the preferred working height 451. As shown in FIG. 8, caregivers are now free to reposition transfer clamp 20 and equipment support structure 200 so it nests closely with hospital bed 410 and the patient's head without disturbing the connections between patient and patient care apparatus. Articulation of transfer device 20 by rotation of cone arms 150 on docking cone axes 460 and bed post axis 461b permits nursing staff to minimize the combined footprint of mobile support platform 400 for efficient and safe transport, in tandem with the patient care apparatus 201, through doorways, corridors and elevators.

In the preferred embodiment, as shown in FIGS. 17-24, transfer device 20 is an assembly of two essentially identical but mirrored housing halves 22 and 23 that are joined along central joint plane 34 and fastened together by screws 42 to form a generally hollow, thin-walled clamshell housing 21 suitable for cost-effective molding or casting. Each housing half 22, 23 has generally smooth, easy-to-clean exterior surfaces 35 comprising label recesses 25 to permit covering assembly screws 42 and other surface irregularities with labels 43 to seal crevices for effective infection control. The interior surfaces 36 of housing halves 22, 23 comprise bosses, ribs and other features that cooperate to retain and fasten pivot pins 26, assembly screws 42, fasteners on which to anchor springs 27 as well as other structural and/or functional elements such as docking cups 60 and support post 41.

Support post 41 is retained by saddle bosses 38, shaped to conform to the outside diameter of support post 41, between first and second housing halves 22, 23, preferably in coaxial relationship with upper docking cup axis 462. Assembly screws 42 are installed to rigidly attach support post 41 to the clamshell housing 21. Support post 41 protrudes from the upper end 33 of clamshell housing 21 to rotatably engage equipment support structure 200.

Figure 19:
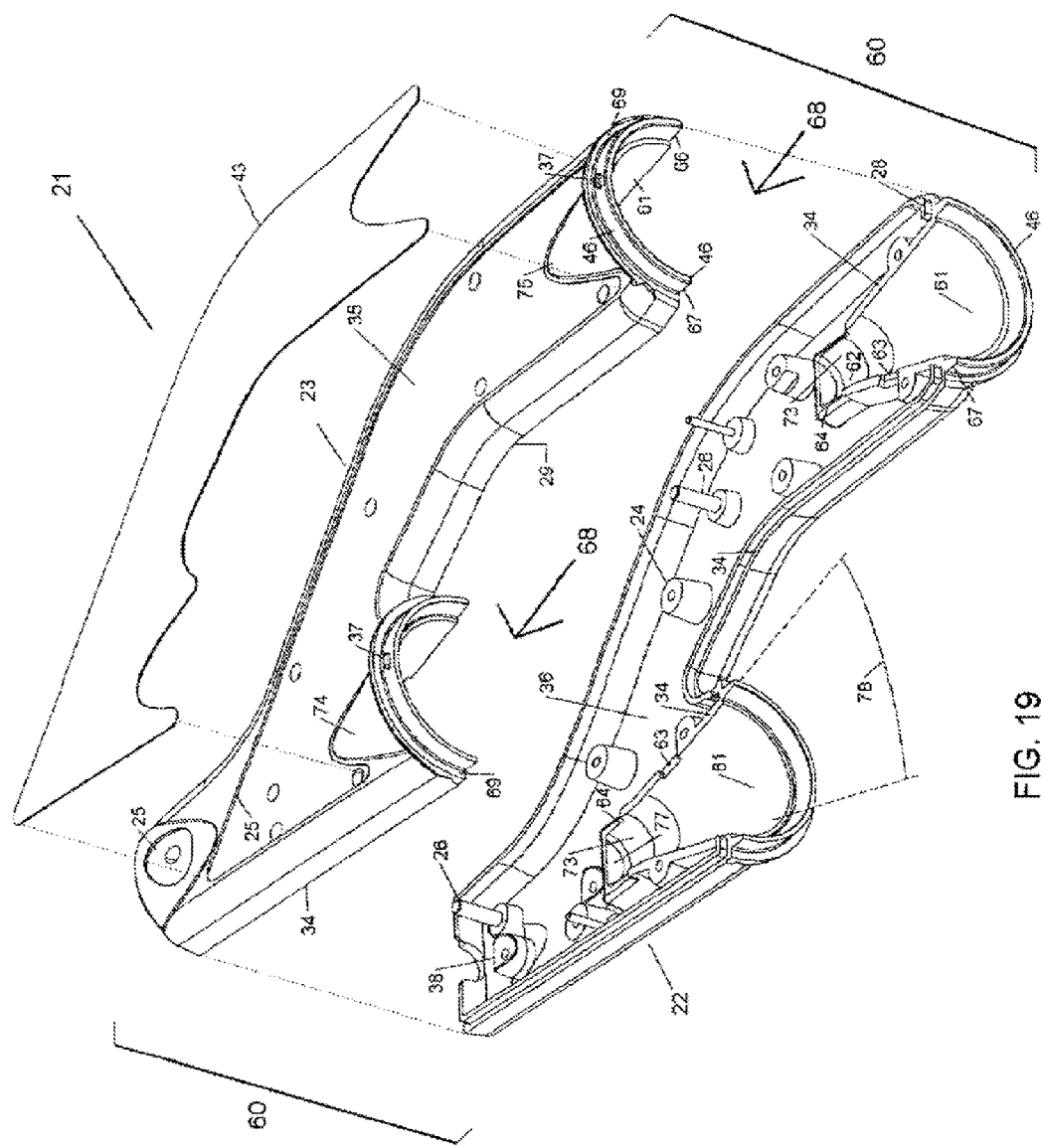
FIG. 19 is a perspective exploded view of the transfer device of the present invention.

As shown in FIG. 19, docking cups 60 are constituted by matching up generally identical but mirrored depressions in the first and second housing halves 23, 24 when the two housing halves are joined to form clam shell housing 21. Upper and lower docking cup axes 462, 463 coincide with the central joint plane 34 of clamshell housing 21 and are generally parallel to each other. Each docking cup 60 constitutes a generally conical cavity 61, with an elongated, cylindrical extension 73 configured to receive docking cone 100 in coaxial alignment.

As shown in FIGS. 19-22, docking cup openings 68 (indicated by arrow 65) face downward and are positioned in the two housing halves 22, 23 such that they are open to the outside for insertion of docking cones 100 without exposing security mechanism 120. Docking cup axes 462 and 463 of the upper and lower docking cup are spaced apart horizontally by cup axis spacing 45. In the preferred embodiment, cup axis spacing 45 is a two to two-and-a-half multiple of the outer ring diameter 278 of docking ring 275 to provide adequate horizontal spacing so users may align docking cones 100 with the respective docking cups 74 and 75 and carry out the docking maneuver with minimal risk of collision or interference between upper and lower cone arms 150 during transfer.

Preferably, the lower docking cup 75 is disposed along bottom cup edge 30 of transfer device 20, and the upper docking cup 74 is positioned higher. Vertical cup spacing 40 between upper and lower docking cups 74 and 75 preferably is approximately equal to the overall cone height 185 to enable docking in case the cone arms of stationary and mobile platforms 300, 400 cross over. Vertical cup spacing 40 assures that users may potentially rotate the transfer device through a full 360 degree rotation when docked on the lower docking cup axis 463 and not otherwise obstructed by hospital bed 110 or other extraneous structures. In the preferred embodiment, vertical cup spacing 40 is approximately 6.75 inches but, depending on specific requirements, may be larger or even zero with both docking cups aligned on the same horizontal plane.

The preferred embodiment of the present invention describes docking cups 60 with cup openings 68 that are open toward the bottom, and docking cones 100 that have their narrow end facing up. While there are advantages regarding security and infection control for this orientation of docking cups and docking cones, upward-opening docking cups and downward-pointing docking cones are within the scope of this invention.

Figure 17:
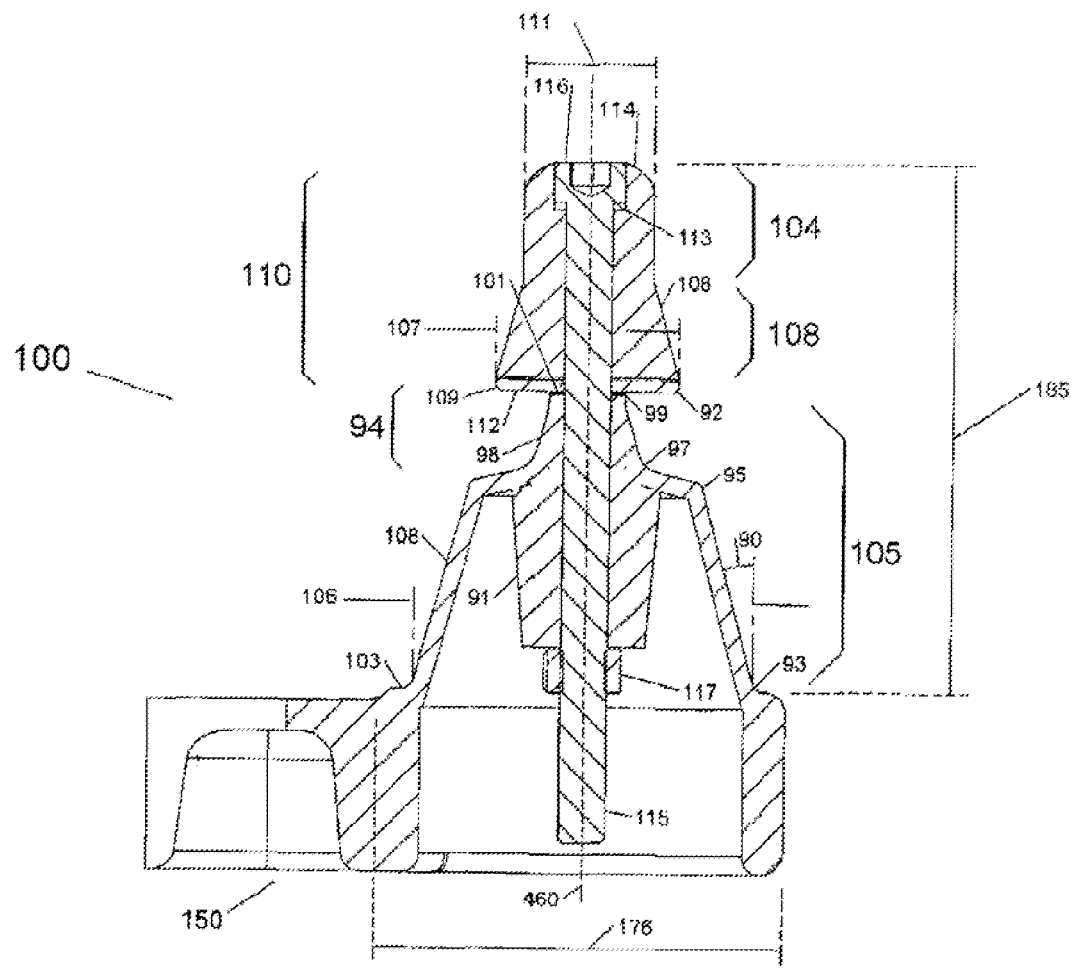
FIG. 17 is a sectional side view of a docking cone taken along line A-A' of FIG. 3.
Figure 18:
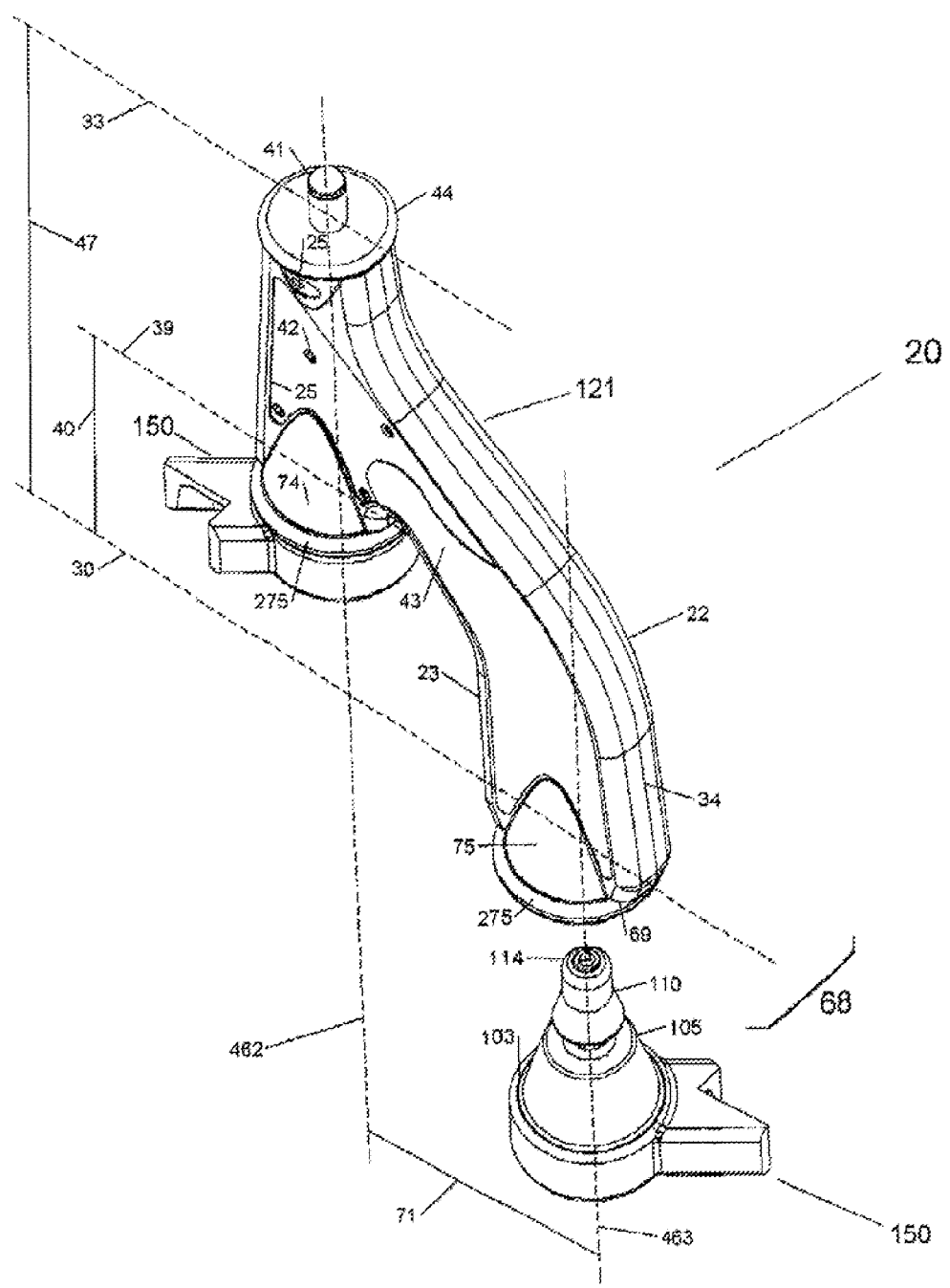
FIG. 18 is a perspective side view of a transfer system with mobile and stationary support platforms partially cut away.
Figure 23:
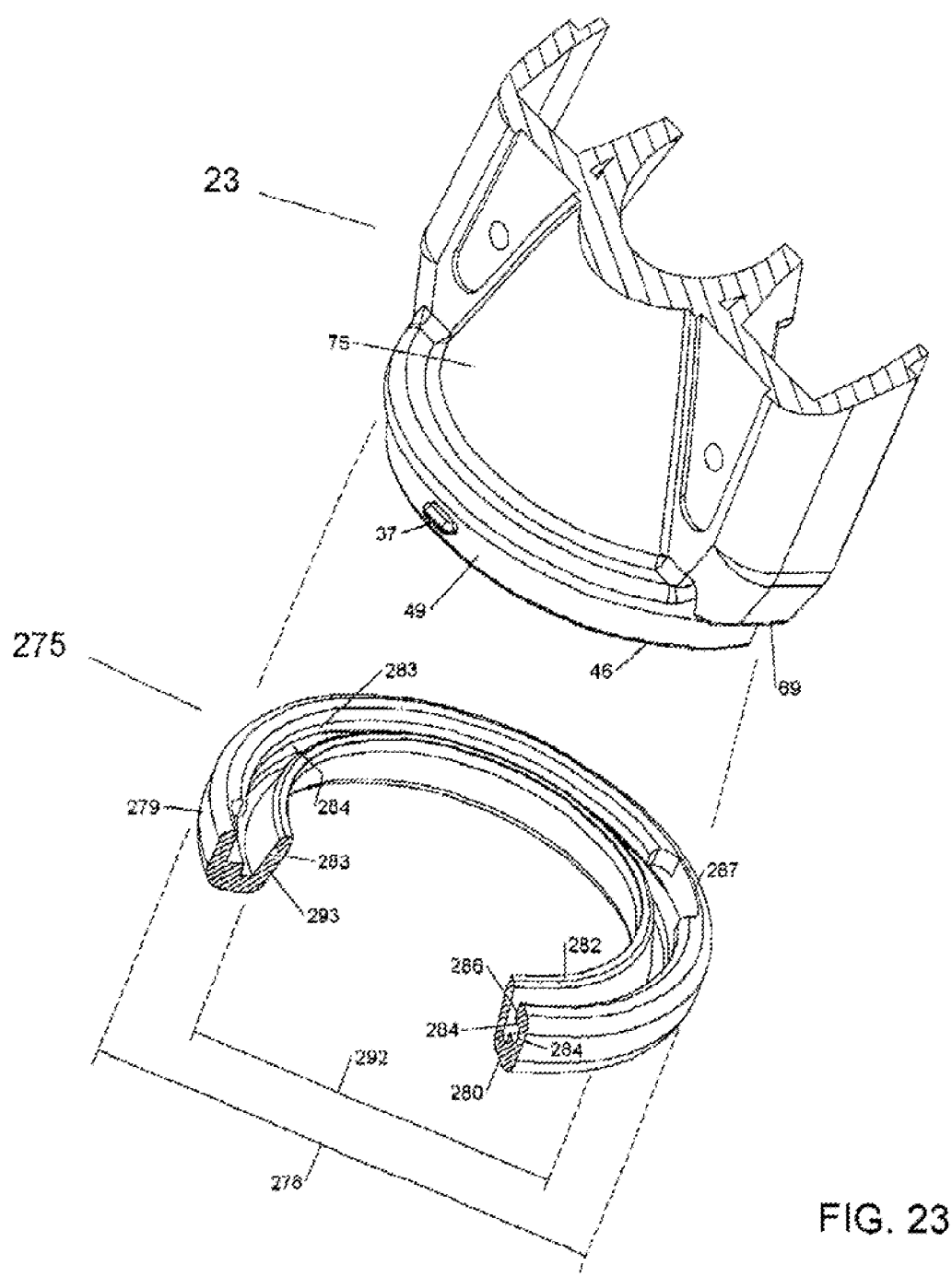
FIG. 23 is an exploded perspective view of a docking ring and a second housing half, with both the docking ring and the second housing half partially cut away.

Docking rings 275 preferably generally are toroid bodies that terminate, reinforce, and provide accurate concentricity to, support flanges 46 of the upper and lower docking cups 74, 75 at cup openings 68. Docking rings preferably are made from a high-strength material with anti-friction characteristics such as a DELRIN or similar acetal resin, high-density polyethylene or other engineering plastics and guide and support transfer device 20 on docking cones 100 during the docking maneuver. As shown in FIG. 23, docking ring 275 has an upper support surface 282 that is in contact with ring support 69 of first and second housing halves, and a bottom support surface 280 that is in contact with base flange 103 of docking cone 100 when docked to transfer device 20 as shown in FIGS. 17 & 18. Registration groove 283 of docking ring 275 has a tapered inner groove surface 285 and a cylindrical outer groove surface 286, and is sized and positioned to receive ring support flanges 46 that depend from the bottom of ring supports 69 of housing halves 22, 23 and form a coaxial and load-bearing joint between docking rings 275 and cup openings 68. Retaining undercut 284 extends radially from outer groove surface 286 of registration groove 283 and receives keys 37 that project radially from outer faces 49 of ring support flanges 46 when docking ring 275 is connected to cup opening 68. Keys 37 of first and second housing halves 22 and 23 may be introduced into retaining undercut 284 of docking ring 275 though keyways 287 and, upon introduction, docking ring 275 may be rotated on ring support flange 46, with keys 37 in engagement with retaining undercut 284, to secure docking ring 275 to clamshell housing 21 in the manner of a bayonet closure. Bottom support surface 280, base flange fillet 93 and the conical portion 108 of cone base 105 of docking cone 100 are sized to receive the bottom support surface 280 and cone support 293 in concentric, nested and load-bearing relationship. Outer ring surface 279 projects beyond the bottom edges of the docking cup 60 and protects the cup openings 68 against impact and abrasion.

As shown in FIGS. 1, 16, 17 & 25, a first cone arm 150 is attached to stationary support platform 300 and a second cone arm 150 is attached to mobile platform 400, and each cone arm 150 comprises a docking cone 100 at its distal end 174 that is configured for docking engagement in docking cups 74, 75 of transfer device 20.

Docking cone 100 is a frustoconical body, and cone base 105 has a cone base diameter 176 that is substantially equal to distal end arm width 176. Docking cone 150 has a base flange 103 with base flange fillet 93 and transitions into cylindrical portion 104 at its narrow, upper end. Between cone tip 114 and cone base flange 103, the outer surface of conical portion 108 of docking cone 100 steps closer to the cone's central axis 111 to form security notch 94. Notch lower edge 95 and cone base upper end 99 demise the lower and upper edges, respectively, of security notch 94. The outer diameter of plate support surface 101 at cone base upper end 99 is substantially smaller than upper base diameter 107 of conical portion 108 of upper cone 110, and engagement plate 109 may be positioned, in coaxial relationship, between plate support surface 101 and the bottom surface of conical portion 108. Security mechanism 120 engages security notch 94 in the secured cone position 130, and notch upper edge 92 of engagement plate 109 protects the upper cone 110 against damage from security levers 121, 122. Engagement plate 109 is a washer, preferably made from steel with an outside diameter that is substantially equal to upper base diameter 107 of upper cone 110. Notch fillet 97 and notch portion 98 form the transition between plate support surface 101 and notch lower edge 95 to provide a space for engagement of security latches 126, 127 during activation of security mechanism 120. Upper cone 110 preferably is made from a tough engineering plastic including a DELRIN or similar acetal resin, high-density polyethylene or any other structural material with low friction characteristics and is fastened to cone base 105 by cone bolt 115 in concentric relationship with docking cone axis 460. Cone bolt head 116 is recessed into cone tip recess 113 of upper cone 110 to form a continuous, smooth cone tip 114. Cone bolt 115 optionally may be inserted from below and in threaded engagement with a blind, internally threaded hole (not shown) in cone tip 114. In the preferred embodiment, cone bolt 115 penetrates cone bolt holes 118 of upper cone 110, engagement plate 109 and inner cone boss 91 of cone base 105. Retaining nut 117 is threaded onto cone bolt 115 and tightened against inner cone boss 91 to assemble upper cone 110, engagement plate 109 and cone base 105 into a strong, load-bearing docking cone 100. To facilitate low-cost manufacturing of cone arms 150 and docking cones 100, processes such as molding or casting may be employed and therefore security notch 94 preferably is created by an assembly of easily fabricated parts rather than as a single part where security notch 94 may be an undercut. However, docking cones 100 may also be formed as a single part. Cone base 105, preferably made from metal such as aluminum or other structural materials, may be cast together with cone arm 150 in one piece or assembled from separate components 105, 150 by welding, mechanical fasteners or other known joining methods.

As shown in FIGS. 20-22 & 25, when the docking maneuver is initiated, docking cone 100 may not be fully engaged in docking cup 60. Docking cup 60 and docking cone 100 cooperate during docking to minimize negative consequences of misalignment between docking cone axis 460 on the one hand and arm connector axis 461a and/or bed post axis 461b on the other hand, as may be expected in the real-life hospital environment, and to enable users to easily target the cone tip 114 of docking cone 100 for entry into docking cup 60. During the transfer maneuver, cone tip 114 progressively slides up along the inner surface of conical cavity 61 inside of docking cup 74 or 75, until cone tip 114 enters cylindrical extension 73 of docking cup 60. During the docking maneuver, the external surfaces of the external base 105 and the upper cone 110 are in contact with, and progressively slide up along, the conical inner contour of the bottom support surface 280 of docking ring 275.

The inner surface of conical cavity 61 of docking cups 74 and 75 is sized and shaped to be generally concentric and coaxial with the tapered external wall of conical portion 108 of cone base 105, and with the tapered external walls of upper cone 110. The conical cavity 61 has a cylindrical extension 73 that is generally concentric with, and sized to receive, cone tip 114. The inner conical contour 280 of docking ring 275 has a control diameter 292 that is substantially equal to the cone base diameter 106, and shaped to be supported by the conical exterior walls of cone base 105 and base flange fillet 93, when fully docked to docking cone 100 in coaxial, load-bearing relationship with either upper docking cup axis 462 or lower docking cup axis 463.

In the preferred embodiment, contact between docking cone 100 and docking cups 74, 75 is restricted to designated structures with low-friction characteristics in order to control friction and wear. When docking cone 100 and docking cups 74, 75 are fully docked, cone tip 114 is in substantial coaxial and concentric engagement with the cylindrical bore 62 of cylindrical extension 73, and cone tip 114 is in substantial sliding contact with inner end surface 77 of cylindrical extension 73. Also, when fully docked, cone tip 114 is in sliding contact with the inner surface of cylindrical bore 62, and base flange 103 and base flange fillet 93 of docking cone 100 are in substantially concentric sliding contact with upper support surface 202, bottom support surface 280 and cone support 293 of cone ring 275, thereby creating a contact-free clearance space 79 by which abrasion-sensitive surfaces are separated.

Figure 20:
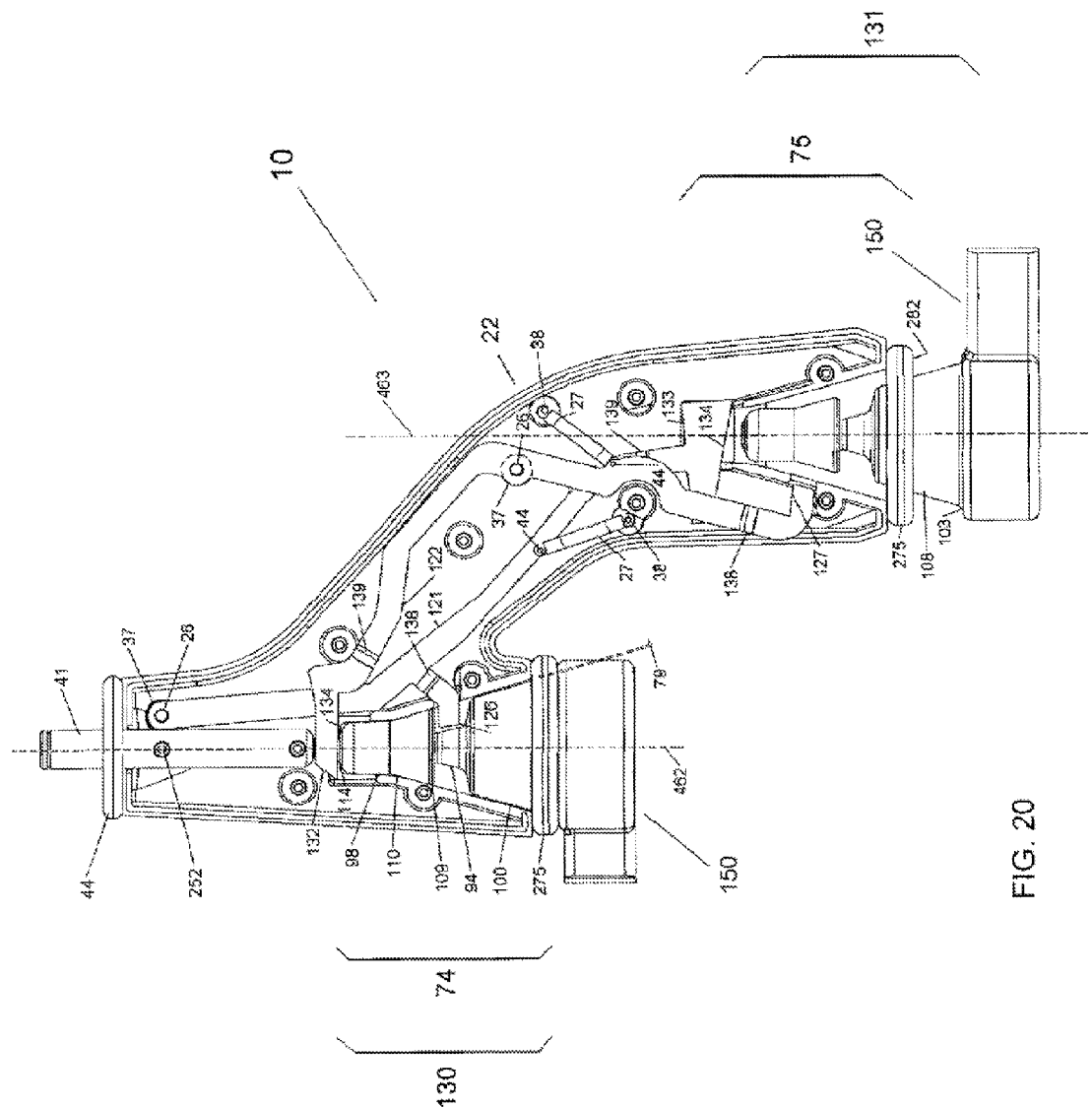
FIG. 20 is a side view of the transfer system with mobile and stationary support platforms partially cut away, the transfer device shown in cross section with a docking cone engaged in the upper docking cup and a lower docking cone disengaged.
Figure 22:
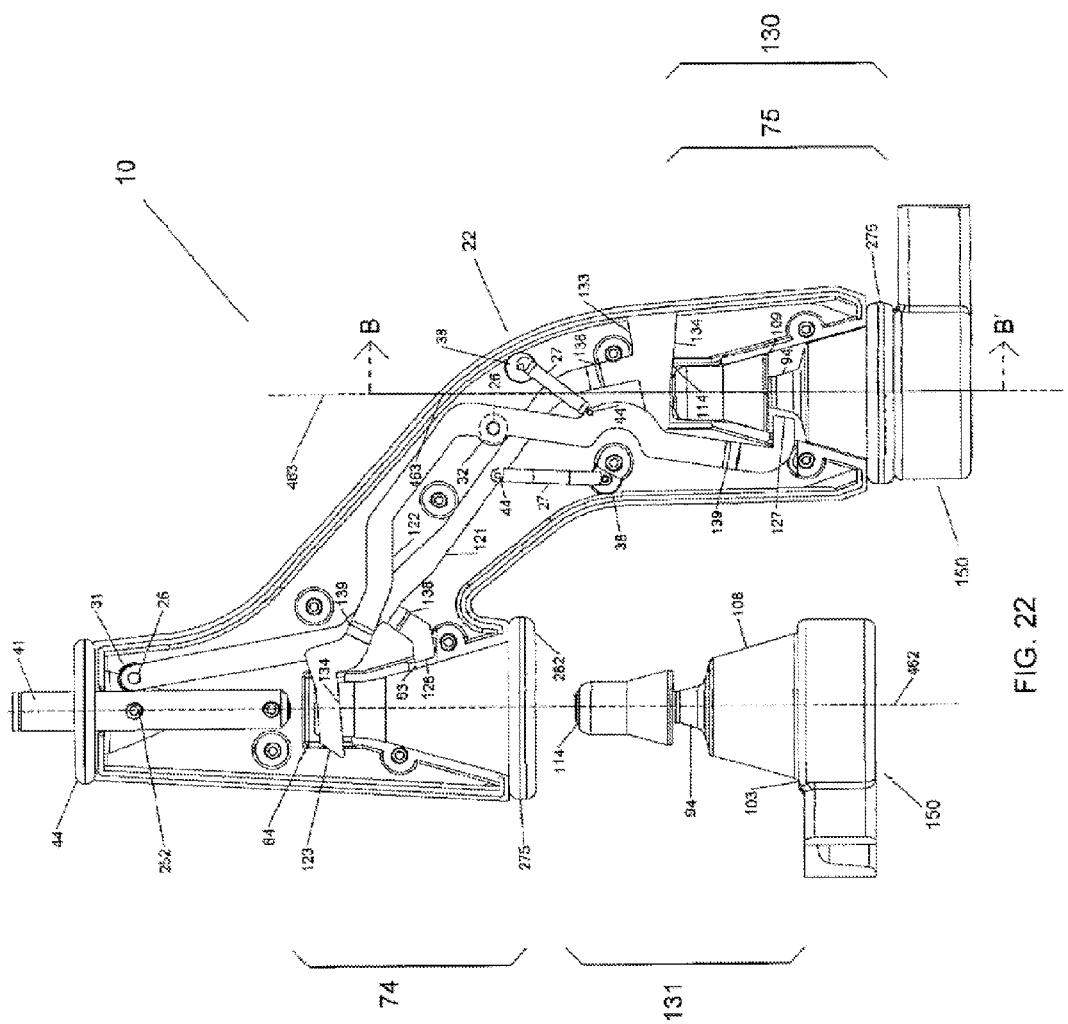
FIG. 22 is a side view of the transfer system with mobile and stationary support platforms partially cut away, the transfer device shown in cross section with a docking cone engaged in a lower docking cup and a docking cone disengaged from an upper docking cup.
Figure 24:
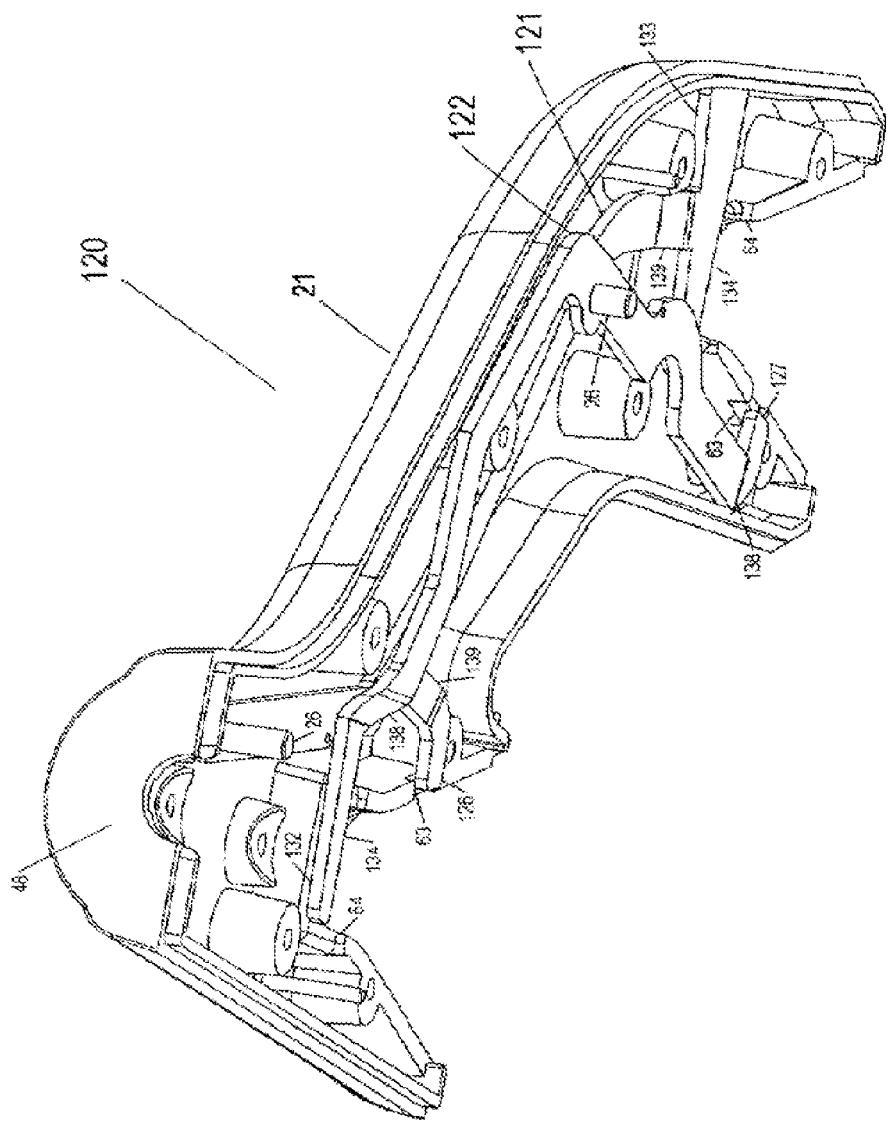
FIG. 24 is a perspective top view of a first housing half with an upper security lever and a lower security lever assembled.
Figure 25:
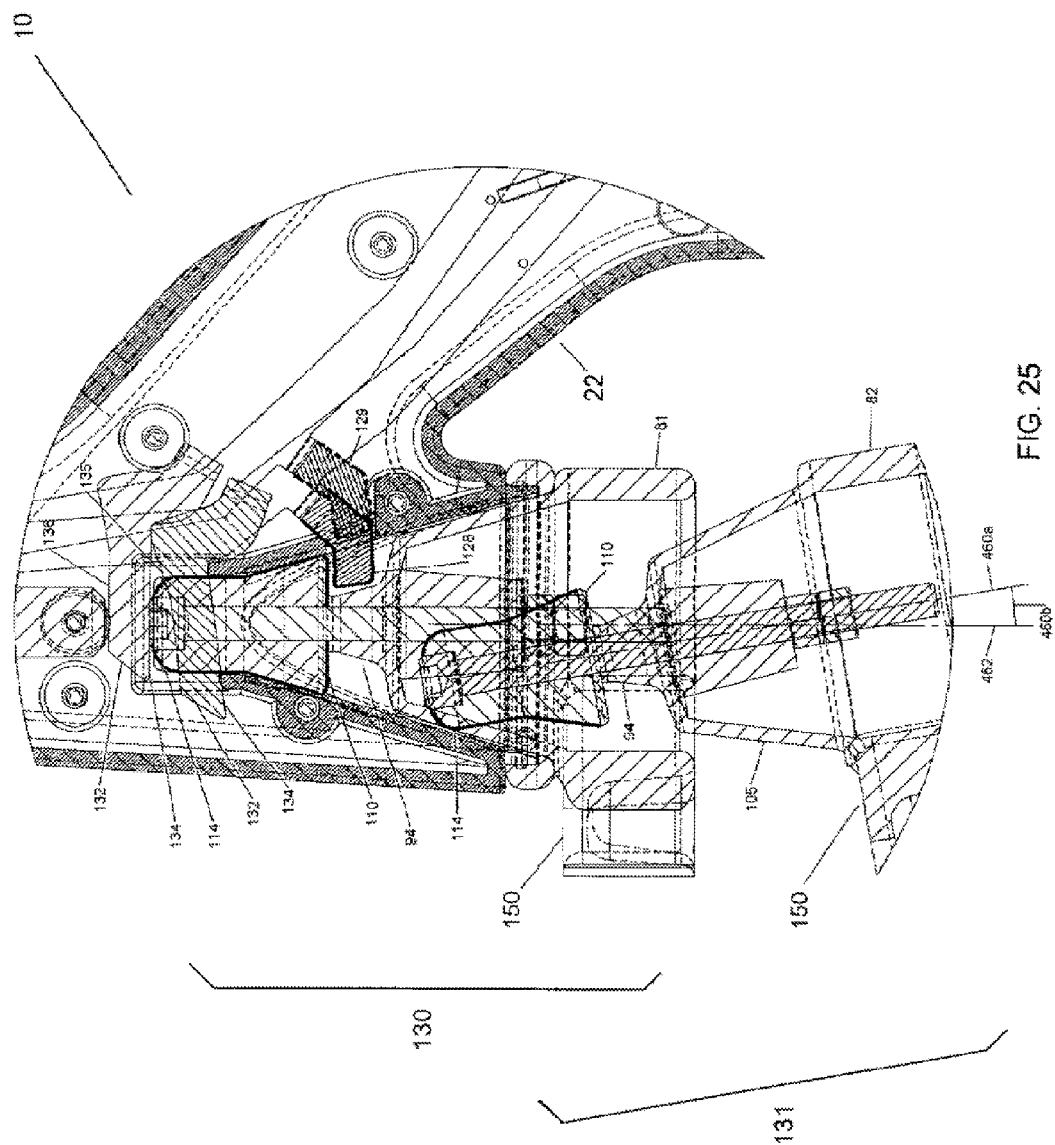
FIG. 25 is a schematic, sectional side view of a transfer device, with the stationary support platform partially cut away, the lower docking cup and equipment support structure cut away, and showing one docking cone docked to an upper docking cup and a second docking cone in misaligned position in preparation of docking, taken along line C-C' of FIG. 5.
Figure 26:
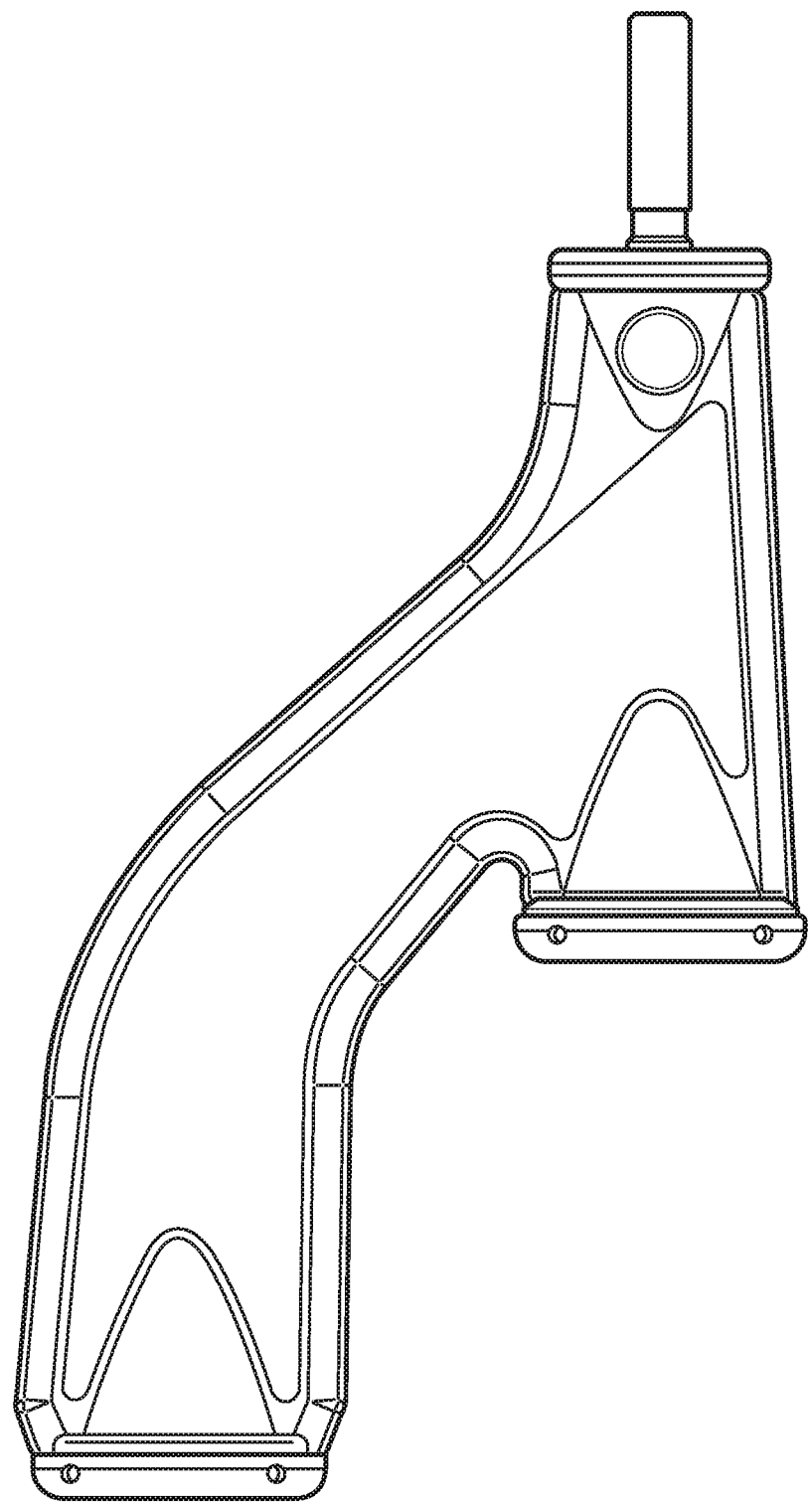
FIGS. 26-32 are various views of a first embodiment of the transfer device of the present invention.
Figure 27:
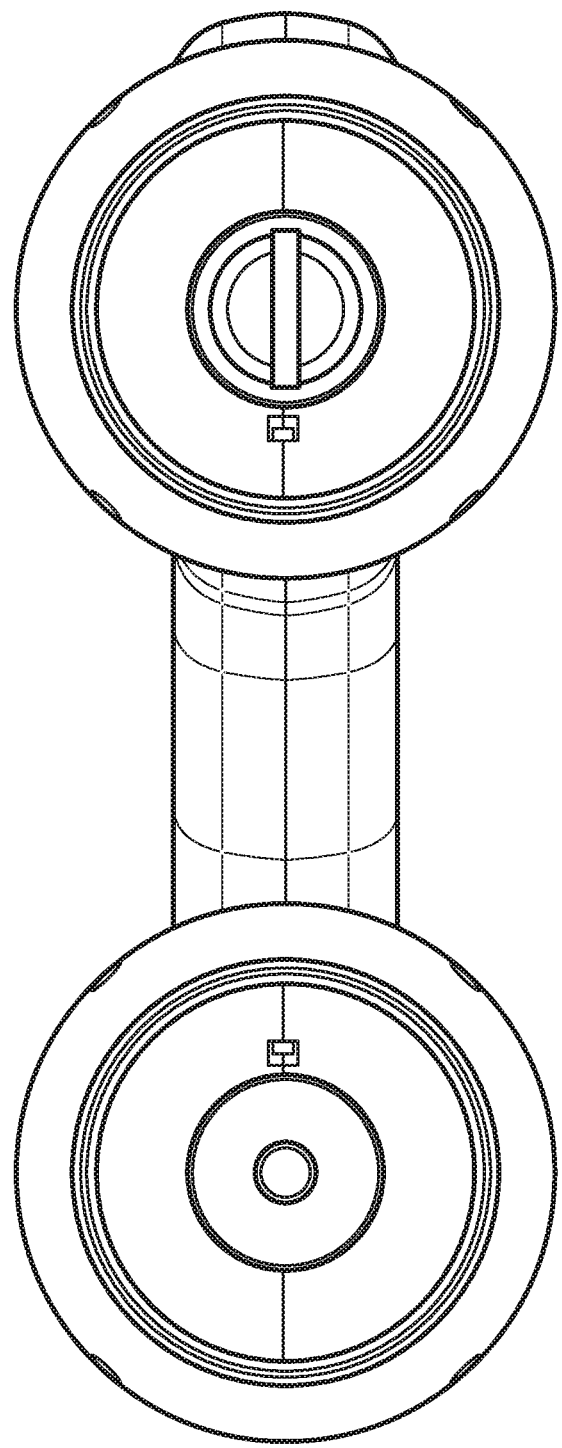
Figure 28:
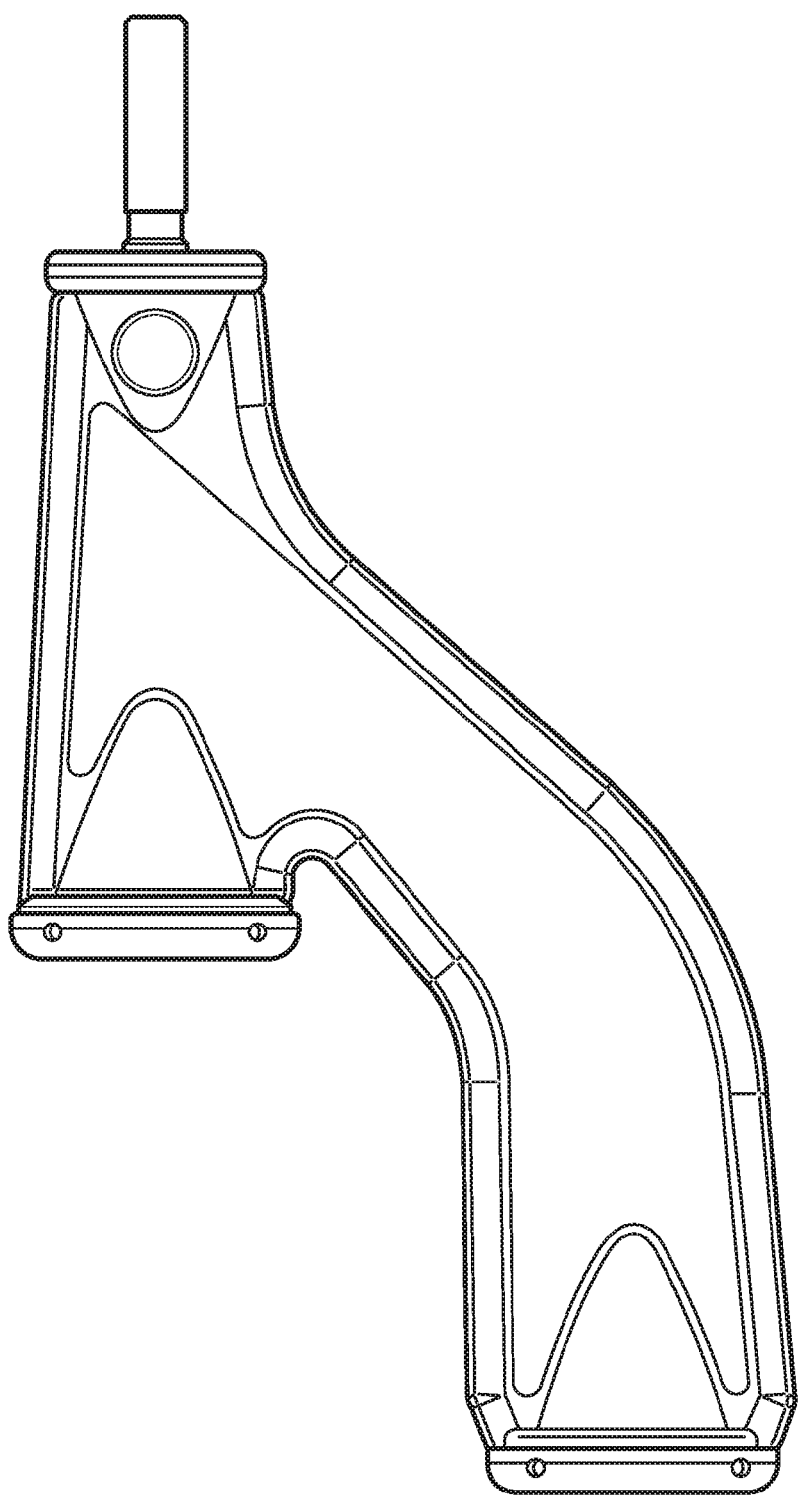
Figure 29:
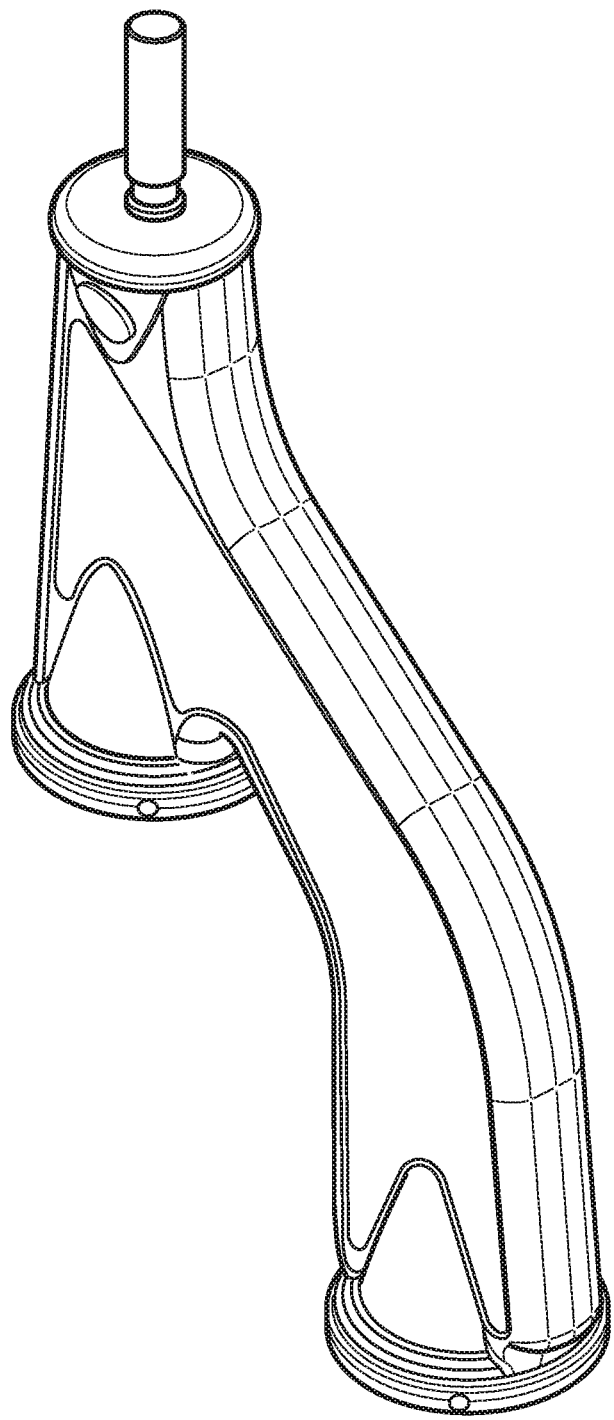
Figure 30:
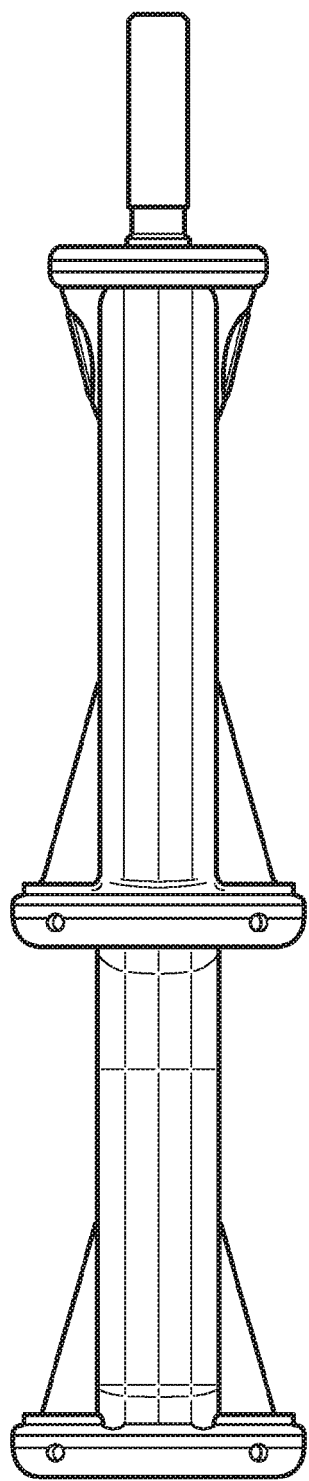
Figure 31:
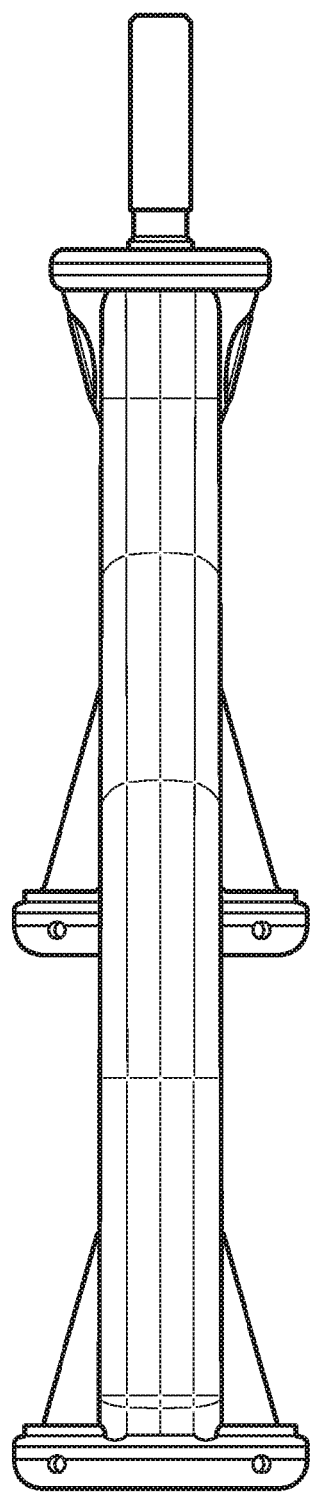
Figure 32:
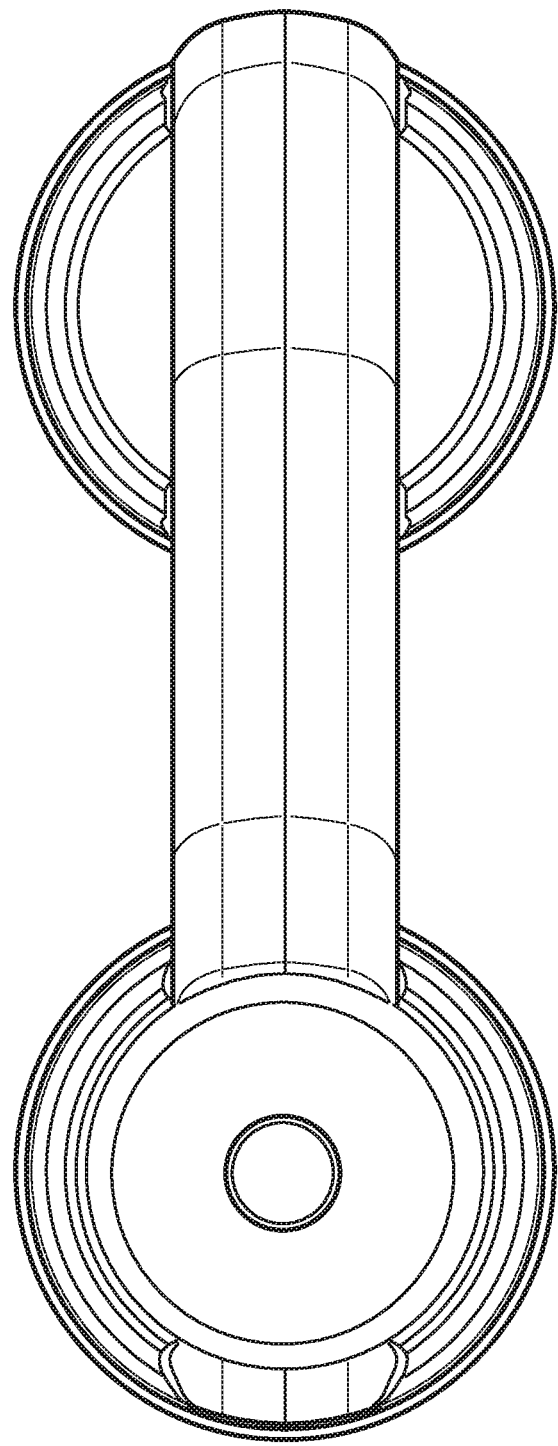
Figure 33:
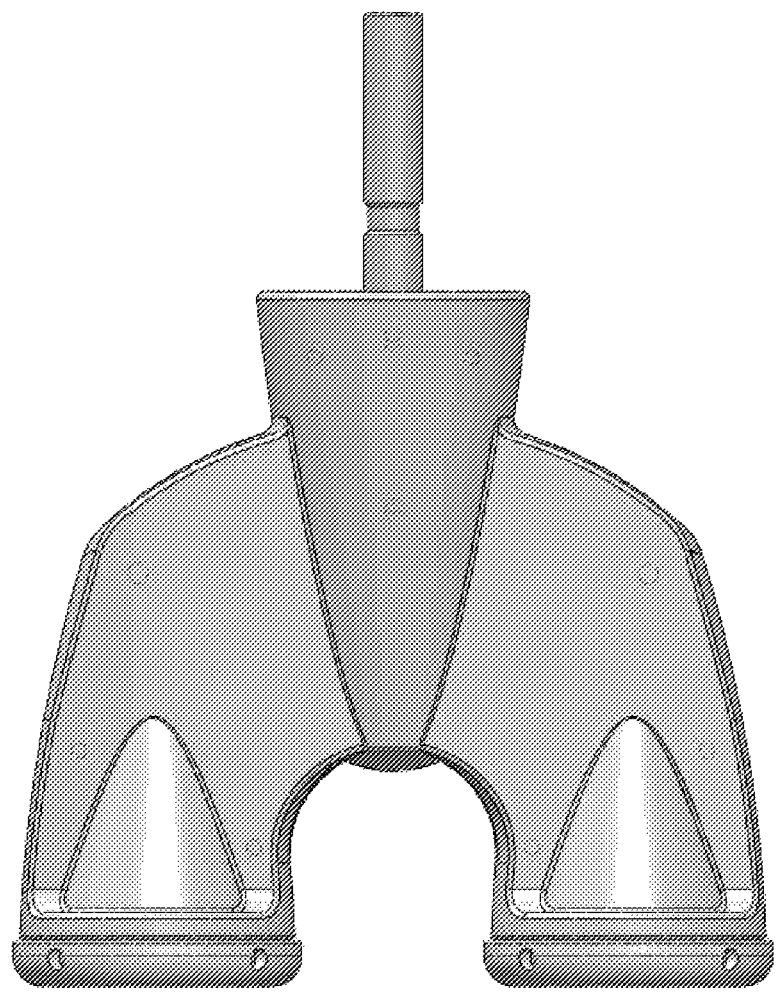
FIGS. 33-39 are various views of a second embodiment of the transfer device of the present invention.
Figure 34:
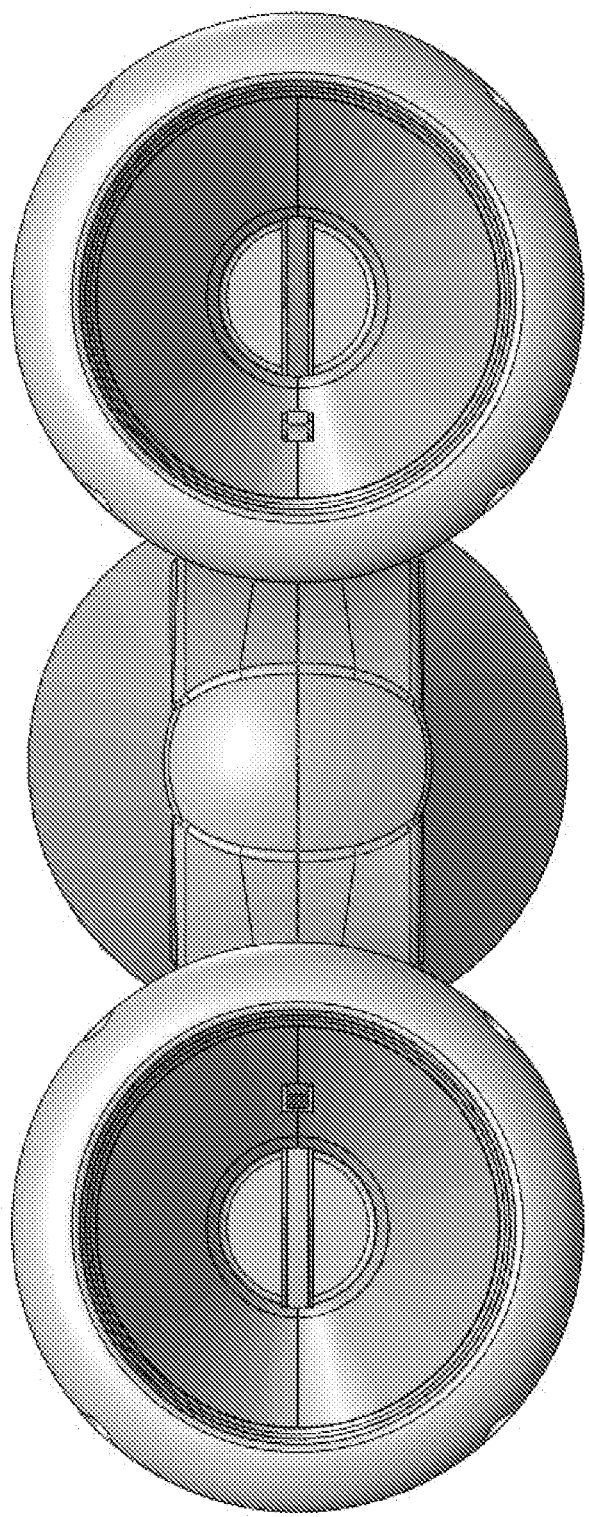
Figure 35:
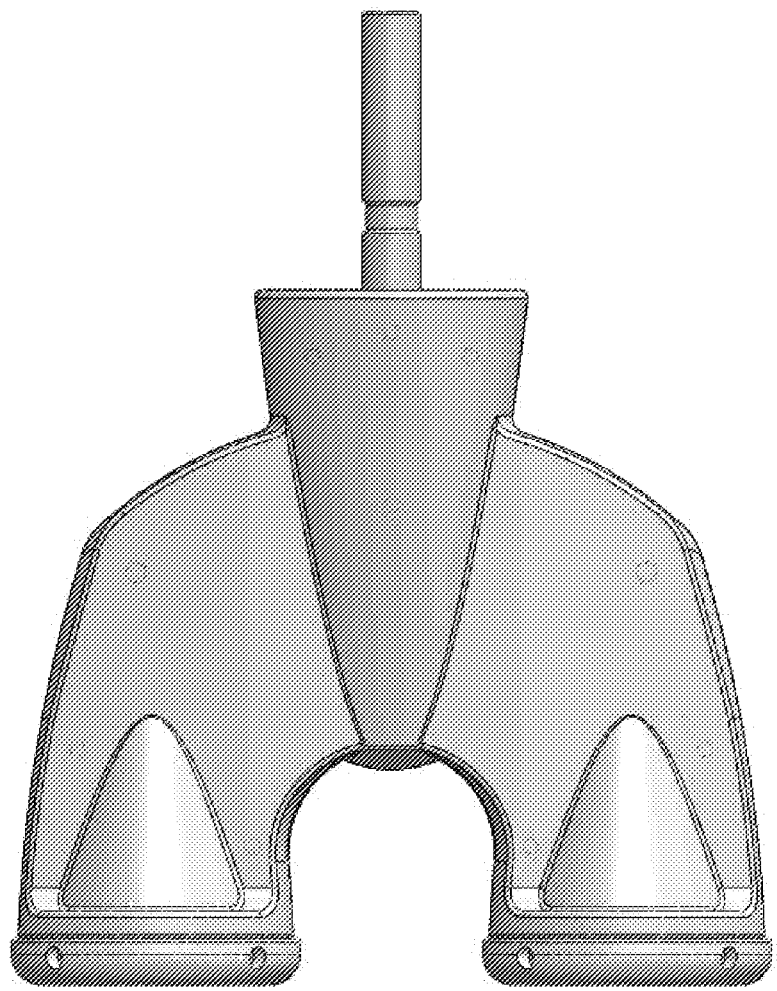
Figure 36:
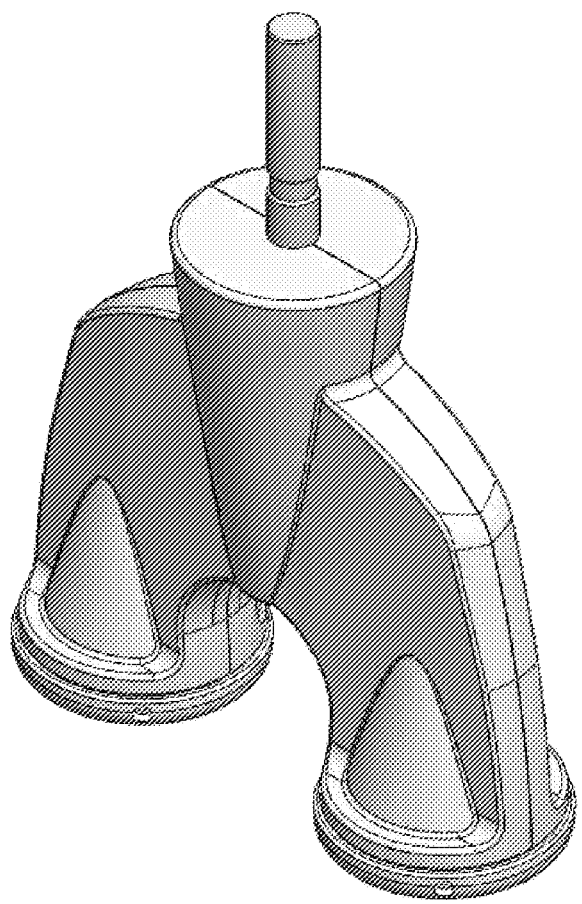
Figure 37:
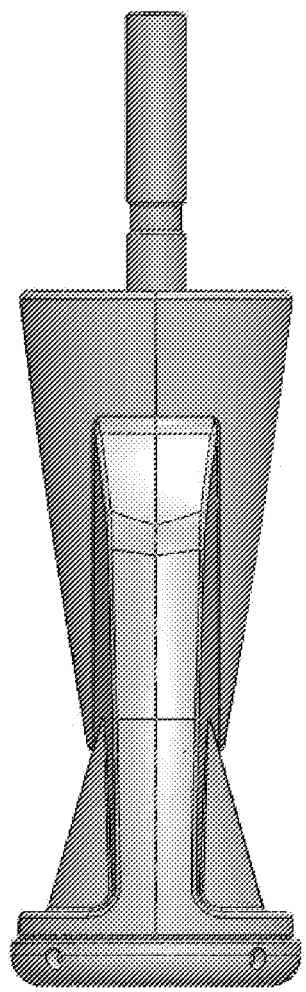
Figure 38:
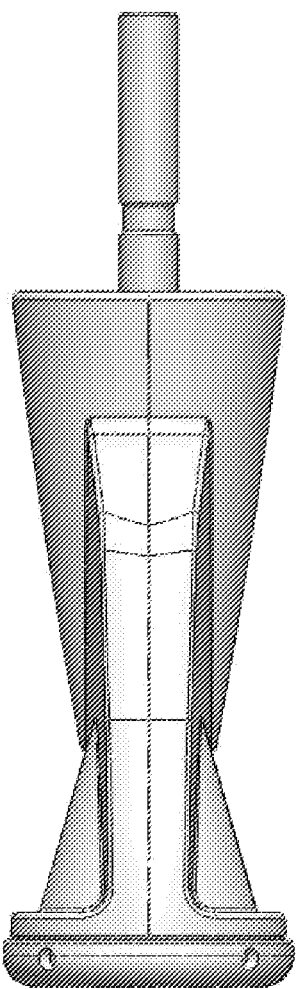
Figure 39:
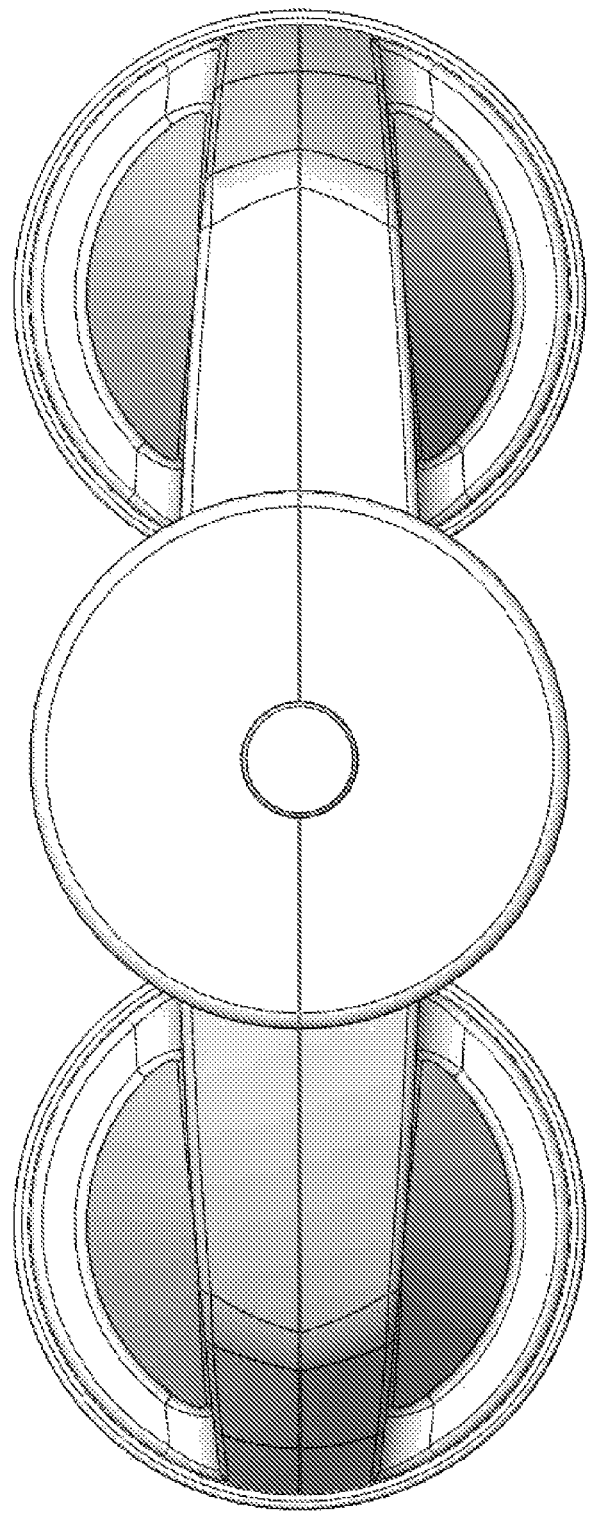
Figure 40:
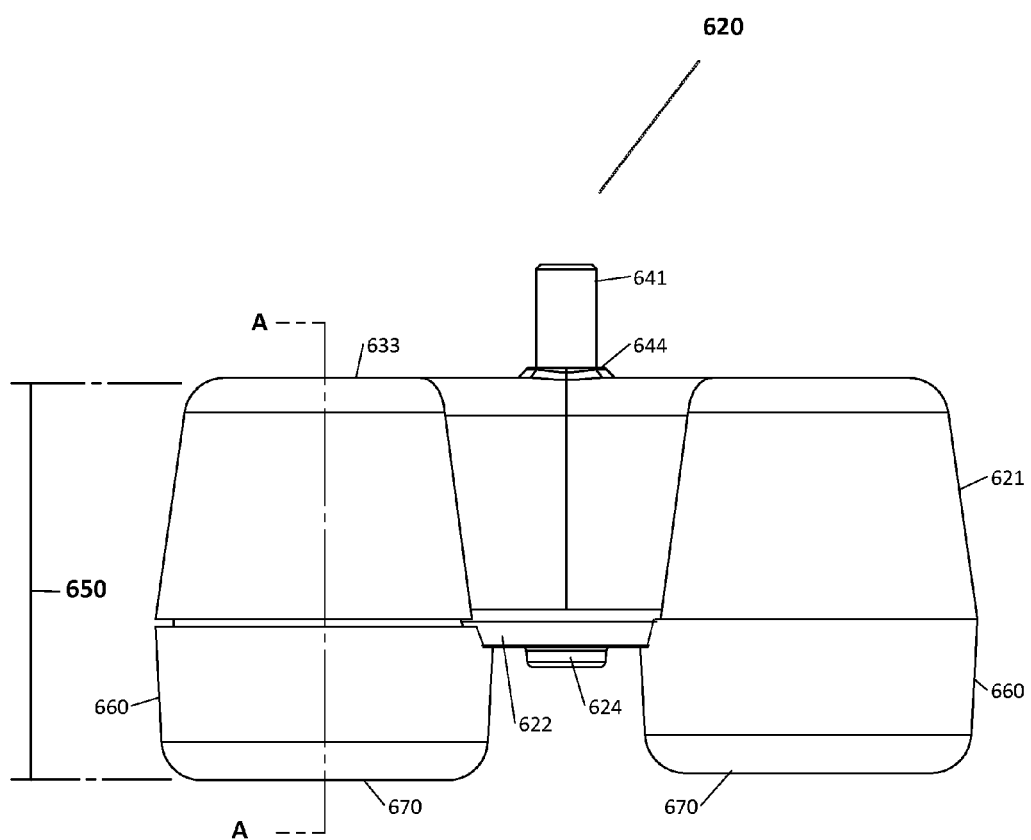
FIG. 40 is a side view of a third embodiment of the transfer device of the present invention.

As shown in FIGS. 20 & 24, security mechanism 120 minimizes the risk of accidentally disconnecting or dislodging transfer device 20 from a docking cone 100 to which it may be docked. Security mechanism 120 is fully enclosed inside of clamshell housing 12. When a first docking cone is in docking engagement with upper docking cup 74 of transfer device 20, transfer device 20 cannot be removed from the first docking cone as long as lower docking cup 75 is not in docking engagement with a second docking cone. With reference to FIG. 22, when a second docking cone is in docking engagement with lower docking cup 75 of the transfer device, transfer device 20 cannot be removed from the second docking cone as long as docking cup 74 is not in docking engagement with the upper docking cup 74. Thus, security mechanism 120 prevents transfer device 20 from being removed from a stationary platform 300 or a mobile platform 400 unless, and only under the condition that, transfer device 20 simultaneously is also fully and securely docked to another support platform to which it is being transferred. Only simultaneous, full docking engagement inside both docking cups 74,75 by two docking cones 100 causes security mechanism 120 to automatically release both the security latches 126 and 127, permitting a caregiver the choice of either releasing the transfer device 20 from the cone arm 100 docked to the upper docking cup 74, or releasing the transfer device 20 from the cone arm 100 docked to the lower docking cup 75. Extracting a first docking cone 100 by a distance of ¼ inch or less from either docking cup 74 or 75 causes the security mechanism 120 to engage the second docking cone, and vice versa, without operator intervention except user activation of the lift mechanism 403 of hospital bed 410 to cause the docking cone 100 attached to the mobile cone arm adapter 413 to be raised or lowered, as the case may be, to control the docking maneuver, as described more fully below. Anyone versed in the art will appreciate that other known means, both manual and powered, may be substituted for the lift mechanism of a hospital bed in order to activate the docking maneuver and security mechanism of this invention.

Upper security lever 212 and lower security lever 122 cooperate with security notch 94 and cone tip 114 of docking cone 100, and with upper and lower docking cups 74 and 75 to retain a docking cone in docking engagement with its respective docking cup. With reference to FIG. 20, when a first docking cone 100 is in docking engagement with upper docking cup 74 and no docking cone 100 is in docking engagement with lower docking cup 60, upper security lever 121 securely retains the first docking cone in docked relationship with transfer device 20. Analogously, with reference to FIG. 22, when a second docking cone 100 is in docking engagement with lower docking cup 75 and no docking cone 100 is in docking engagement with upper docking cup 60, lower security lever 122 securely retains the second docking cone in docked relationship with transfer device 20.

Figure 21:
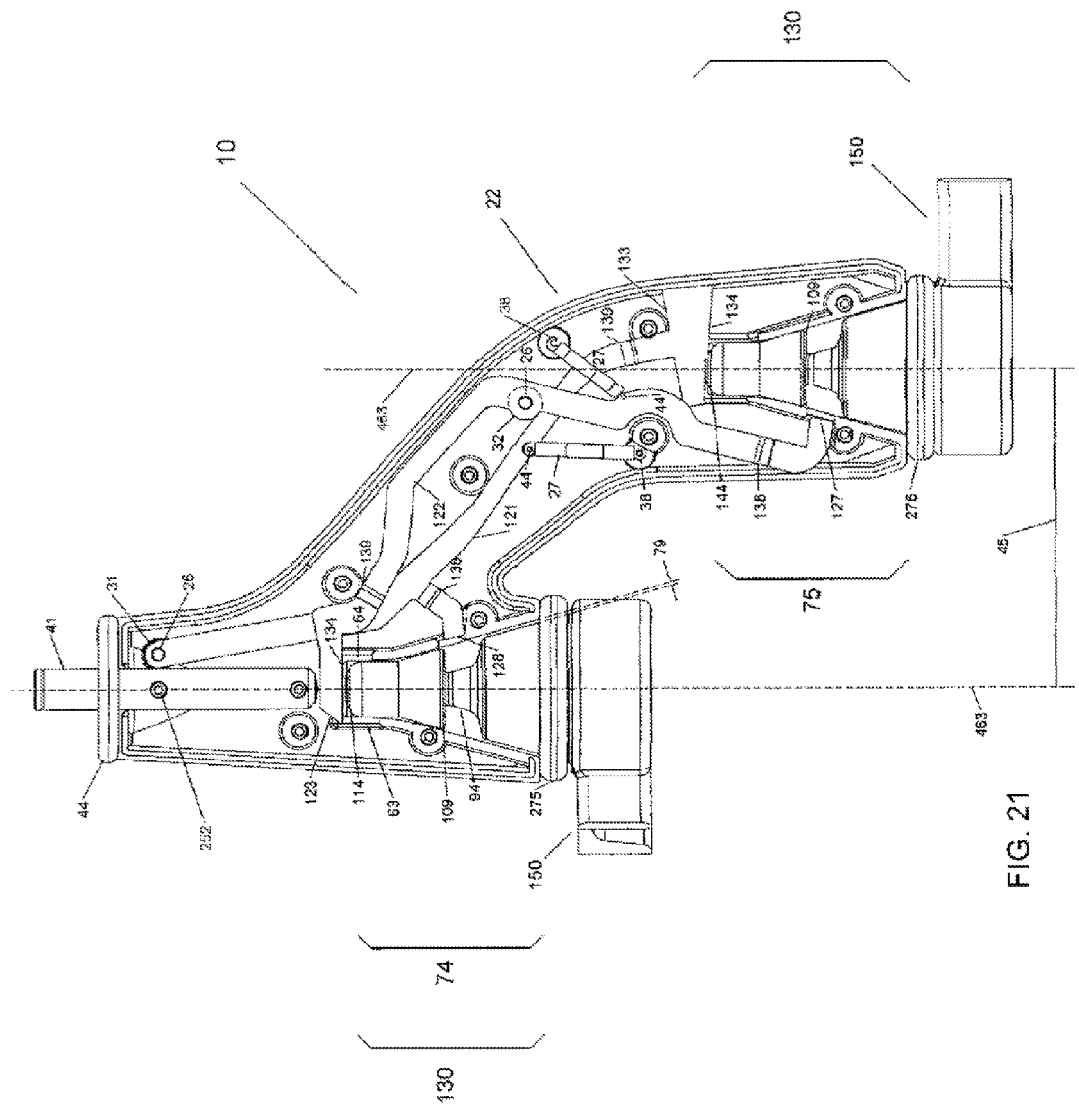
FIG. 21 is a side view of the transfer system with mobile and stationary support platforms partially cut away, the transfer device shown in cross section with a docking cone engaged in a lower docking cup and a docking cone engaged in an upper docking cup during transfer.

Simultaneous full docking engagement of two docking cones 100 in transfer device 20, as shown in FIG. 21, with one docking cone 100 seated in the upper docking cup 74 and the other docking cone 100 seated in the lower docking cup 75, causes upper security lever 121 to release the first docking cone, and security lever 122 to release the second docking cone.

Security levers 121 and 122 have analogous functions and share key structures and features such as a pivot holes 123, security latches 126 and 127, and cone feelers 132 and 133, and are both shaped to clear screw bosses 24 and pivot boss 37, as well as sidewalls and other internal features to avoid collisions when pivoting between secured cone position 130 and released cone position 131. Security levers 121 and 122 preferably are made from sheet steel or other rigid, structural materials.

Pivot pins 124 are trapped between upper and lower pivot bosses 31, 32, respectively, on the inside surfaces 36 of first and second housing halves 22 and 23. Security lever 121 and security lever 122 are both rotatably attached to pivot pins 124 at pivot holes 123 to permit each security lever to pivot between a first secured cone position 130 to a second released cone position 131. Each security lever 121, 122 comprises a security latch 126, 127, respectively, that pivots from a first secured position 130 to a second released position 131, or into and out of engagement with security notch 94 of docking cone 100 to control retention of the docking cone in the respective docking cup of transfer device 20. Each security lever 121, 122 also comprises a security cone feeler 132, 133 that causes security levers 121, 122 to pivot from a first secured cone position 130 to a second released cone position 131 when pivotably displaced by the cone tip 114 of a docking cone 100 during transfer.

In the preferred embodiment, as shown in FIGS. 20-24, upper and lower docking cups 74, 75 are disposed along upper cup edge 39 and lower cup edge 30, respectively, requiring each of the security levers 121, 122 to have a different configuration and shape. Thus, each security latch 126, 127 and each cone feeler 132, 133 is positioned on its respective security lever at a different position in relation to its respective pivot hole 123, as more fully described below.

As shown in FIGS. 21-25, a pivot hole 123 is located at the upper end of upper security lever 121 and a lower cone feeler 133 is located at the bottom end of upper security lever 121. Pivot pin 124 is pivotably attached at pivot hole 123 to upper pivot boss 31 on the interior surfaces 36 of clamshell housing 121, and upper pivot boss 31 is located above upper docking cup 74 and near upper docking cup axis 462. Lower cone feeler 133 depends from upper security lever 121 in an offset relationship by offset 138. Upper security latch 126 is located between pivot hole 123 and lower cone feeler 133 and also depends from upper security lever 121 in an offset relationship by offset 138. Offset 138 causes lower cone feeler 133 and upper security latch 126 to be in coplanar relationship. Lower cone feeler 133 and upper security latch 126 are both sized and positioned to align with docking cone axes 460 when cones 100 are fully docked in upper and lower docking cups 74 and 75 and cooperate with cone tip 114 of docking cone 100 in the lower docking cup 75 and security notch 94 of docking cone 100 in the upper docking cup 74.

As also shown in FIGS. 21-25, lower security latch 127 is located at the lower end of lower security lever 122 and upper cone feeler 132 is located at the upper end of lower security lever 122. Pivot hole 123 is located between the lower security latch 127 and upper cone feeler 132, and is pivotably attached to lower pivot boss 32 on the interior surfaces 36 of clamshell housing 121 by pivot pin 124. Lower pivot boss 32 is located above lower docking cup 75 and near lower docking cup axis 463 and upper cone feeler 133 depends from lower security lever 122. Lower security latch 127 is located below pivot hole 123 and upper cone feeler 132 is located above pivot hole 123, and both lower security latch 127 and upper cone feeler 132 depend from lower security lever 122 in a reverse-offset relationship by reverse-offset 139. Reverse-offset 139 causes upper cone feeler 132 and lower security latch 127 to be in coplanar relationship. Upper cone feeler 132 and lower security latch 127 are both sized and positioned to align with docking cone axes 460 when cones 100 are fully docked in upper and lower docking cups 74 and 75 and cooperate with cone tip 114 of docking cone 100 in the upper docking cup 74 and security notch 94 of docking cone 100 in the lower docking cup 75.

Upper security latch 126 and lower cone feeler 133 are offset from upper security lever 121 in one direction (138) and lower security latch 127 and upper cone feeler 132 are offset from lower security lever 121 in the opposite direction (139). Because upper and lower security latches 126 and 127 as well as upper and lower cone feelers 132 and 133 are coplanar and positioned within the clamshell housing 121 in parallel alignment with, and centered upon, central joint plane 34, upper and lower security levers 121, 122 are positioned on different panes within clamshell housing 21 so that they do not collide when independently pivoting between secured cone position 130 and released cone position 131.

As shown in FIG. 19, latch clearance notches 63 and feeler clearance notches 64 in the first and second housing halves 22 and 23 permit security latches 126 and 127, and cone feelers 132 and 133, to extend into the conical cavities 61 of docking cups 74, 75 where security latches and cone feelers 126, 127, 132 and 133, respectively, are positioned to interact with docking cones 100 that may move into and out of docking relationship with docking cups 74 and 75, as previously described.

Springs 27 are attached between spring anchors 44 of each security lever 121, 122 and spring bosses 38 on housing halves 22, 23 in order to urge each security lever 121 and 122 into its respective secured cone position 130 to provide firm engagement of upper and lower security latches 126, 127 in the respective security notches 94, and position upper and lower cone feelers 132, 133 for activation by a cone tip 144 during docking.

When docking cone 100 is firmly seated in upper docking cup 74, upper security latch 126 is in full engagement with security notch 94 of the docking cone 100 engaged in cup 74. Conversely, when docking cone 100 is firmly seated in lower docking cup 75, lower security latch 127 is in full engagement with security notch 94 of the docking cone 100 engaged in cup 75. If upward force is applied anywhere to transfer device 20 through an accidental collision with an object in the environment or an unauthorized attempt to remove the transfer device from engagement with docking cone 100 to which it is attached, either security latch 126 or 127 engages engagement plate 109 of security notch 94 to interdict extraction of transfer device 20 from the docking cone which supports it.

In an alternate embodiment, as shown in FIGS. 40 to 45, transfer device 620 is an assembly having an upper housing 621, a lower housing 622 and a support post 641 received therebetween. Two substantially identical subassemblies 748 are assembled to, and retained by, upper housing 621 in generally equidistant, parallel and symmetric relationship with support post 641. Docking cups 660 are received in upper housing 621 in substantially parallel relationship with, and generally equidistant from, support post 641 and are seated in the upper housing by means of locking rim 628. Lower housing 622 interdigitates with docking cups 660 by means of registration notches 646. Support post 641 is received in the bottom guide 624 of lower housing 622 and retention opening 644 in the upper end 633 of upper housing 621. Support post 641 protrudes from the upper end of upper housing 621 to rotatably engage equipment support structure 200.

As previously described, docking cups 660 are substantially identical and comprise generally identical conical hollows 661, each having an elongated extension 673 to receive upper cone 710 of docking cone 700 in coaxial alignment, as more fully described below. Bottom openings 680 of docking cups 660 face downward and are positioned such that they are open to the outside for insertion of docking cones 700 without exposing security mechanism 720.

Figure 41:
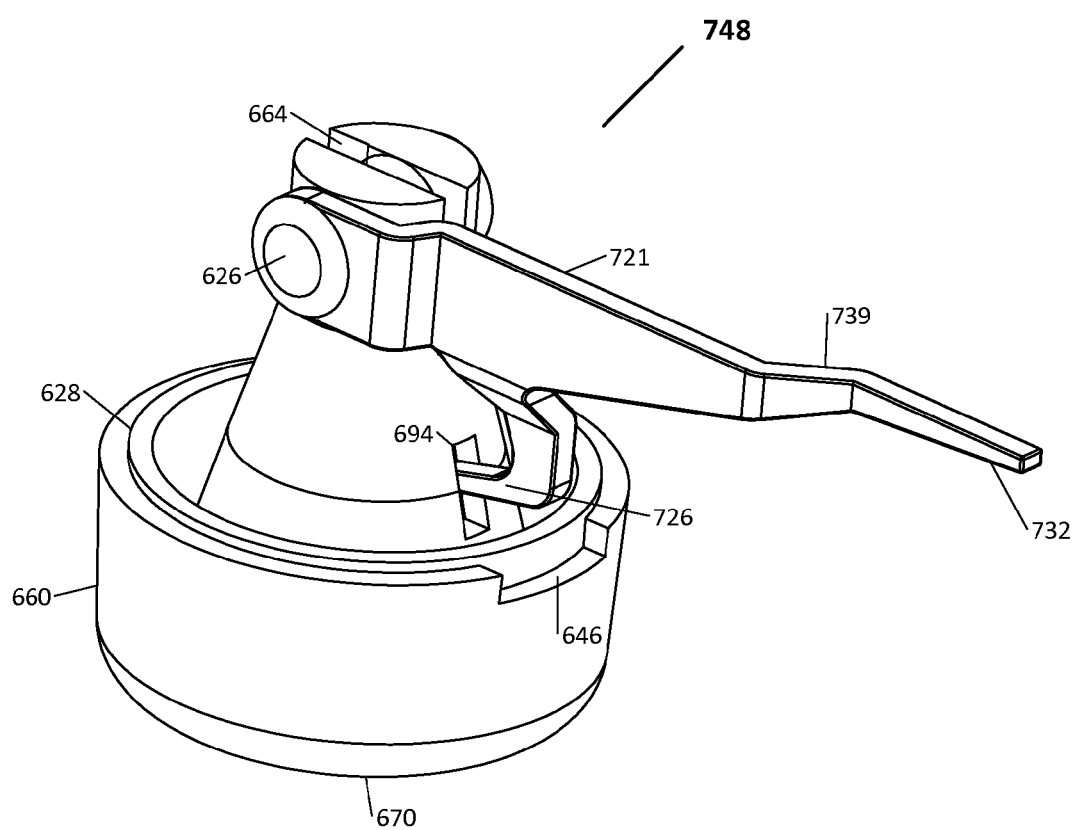
FIG. 41 is an exploded view of one cup of a third embodiment of the transfer device of the present invention with the cover shell removed.
Figure 42:
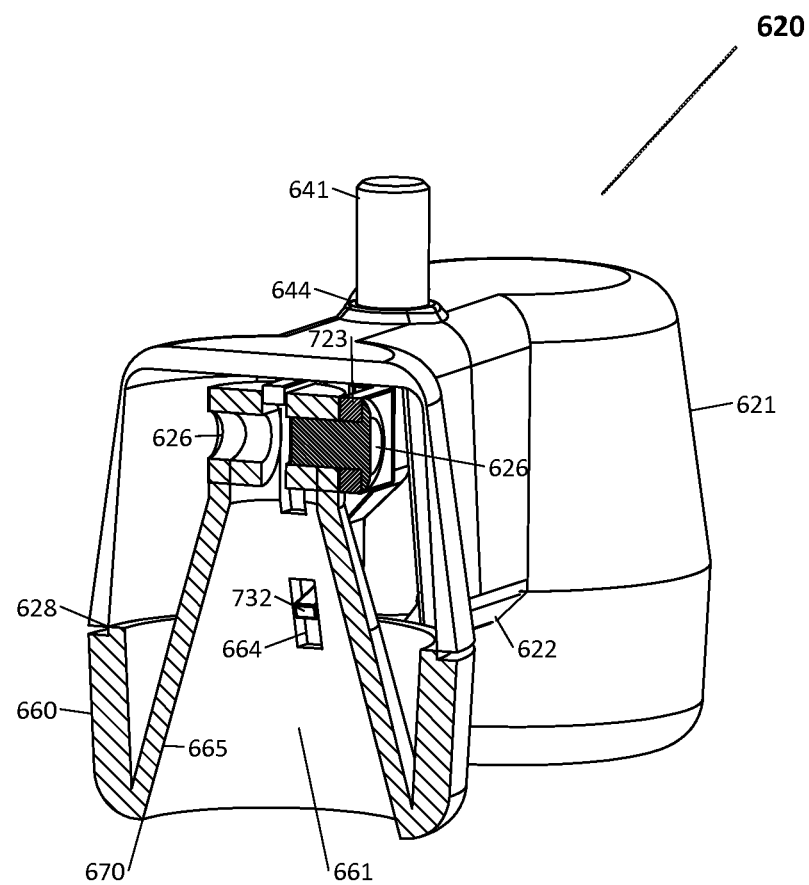
FIG. 42 is a cross sectional view of a third embodiment of the transfer device of the present invention taken along A-A of FIG. 40.
Figure 43:
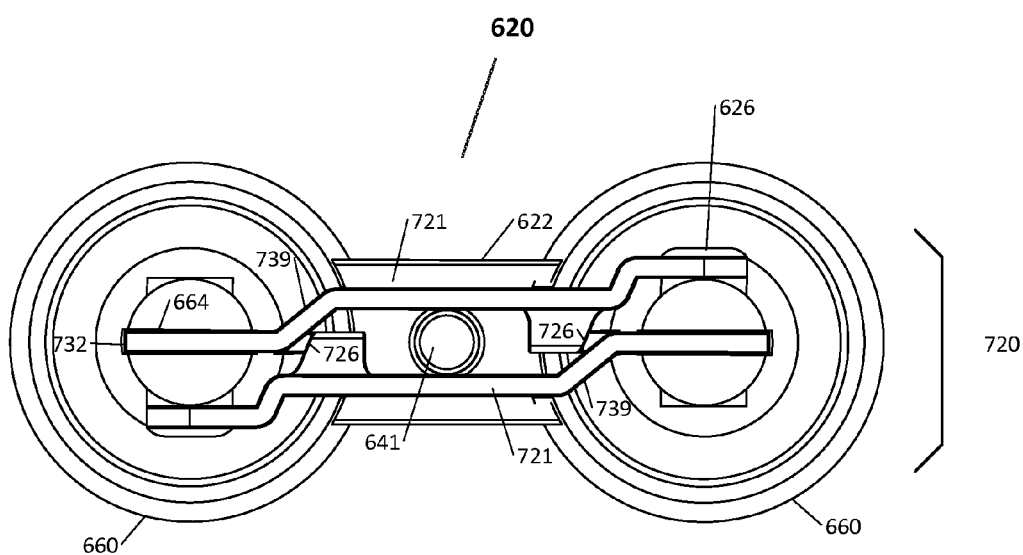
FIG. 43 is a top view of the transfer device with the cover shell removed.
Figure 44:
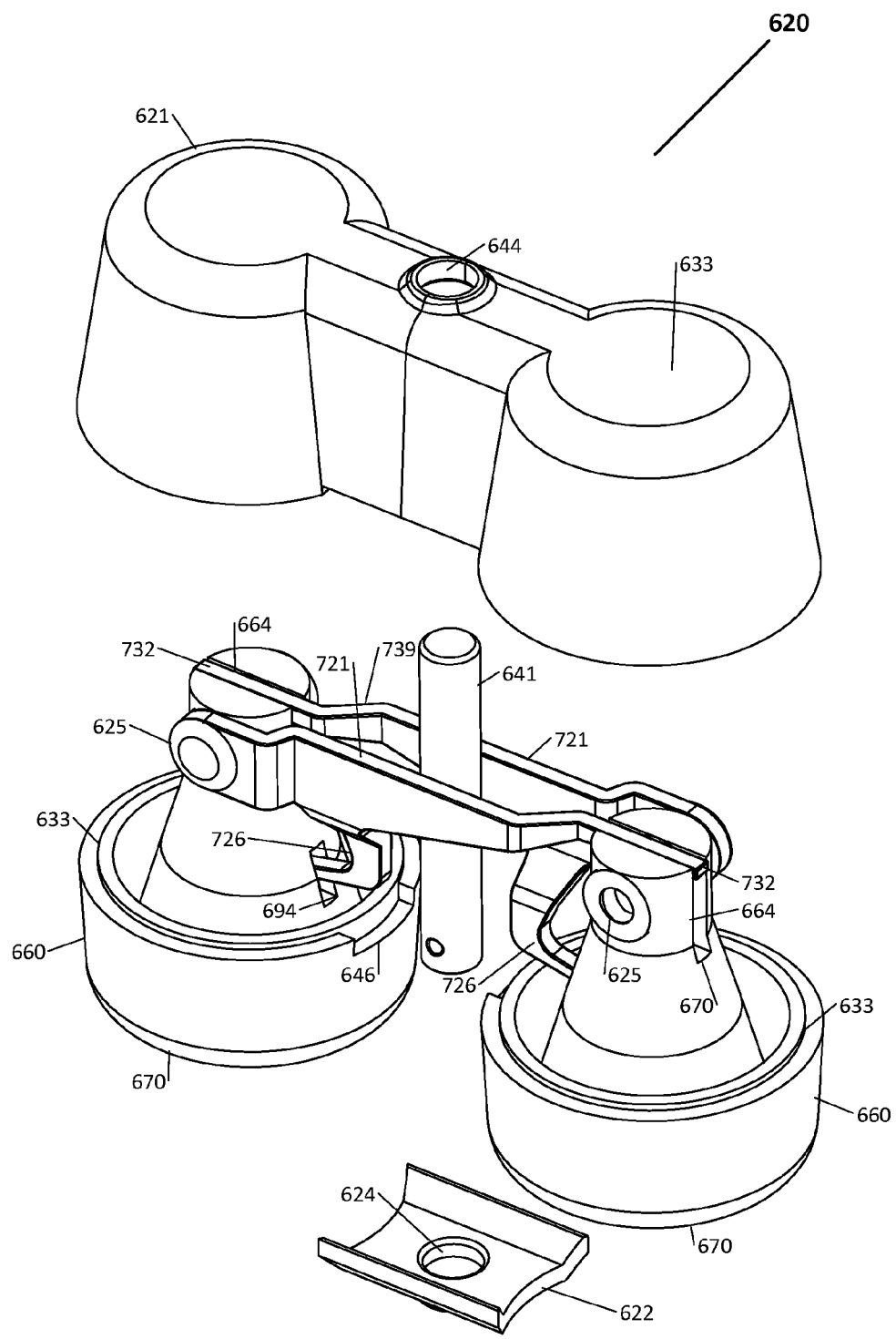
FIG. 44 is an exploded view of the transfer device.

As shown in FIGS. 41 & 42, docking cup 660 preferably is formed as a solid of revolution with an inner conical surface 665 shaped to coaxially receive frustoconical docking cone 700. The docking cup comprises a bottom contour 670 shaped to deflect misaligned insertion of cone tip 711 of upper cone 710; a security notch 694; and a feeler notch 664. Further, docking cup 660 preferably comprises a pivot 626 to pivotally attach security lever 721, thus constituting a self-contained subassembly 748 of a docking cup with integral, pivoting security lever, as shown in FIG. 41. Two substantially identical subassemblies 748 are assembled to, and retained by, upper housing 621 in generally equidistant, parallel and symmetric relationship with post 641.

Each security lever 721 of security mechanism 720 comprises a security latch 726 that pivots from a first secured position to a second released position, or into and out of engagement with security engagement notch 709 of docking cone 700 to control retention of the docking cone in the respective docking cup of transfer device 620. Each security lever 721 also comprises a cone feeler 732 that causes the security latch 726 of said security lever 721 to pivot from a first secured position to a second released position in response to being displaced upward, against the bias of spring 747 (not shown), by the cone tip 711 of docking cone 700.

Figure 45:
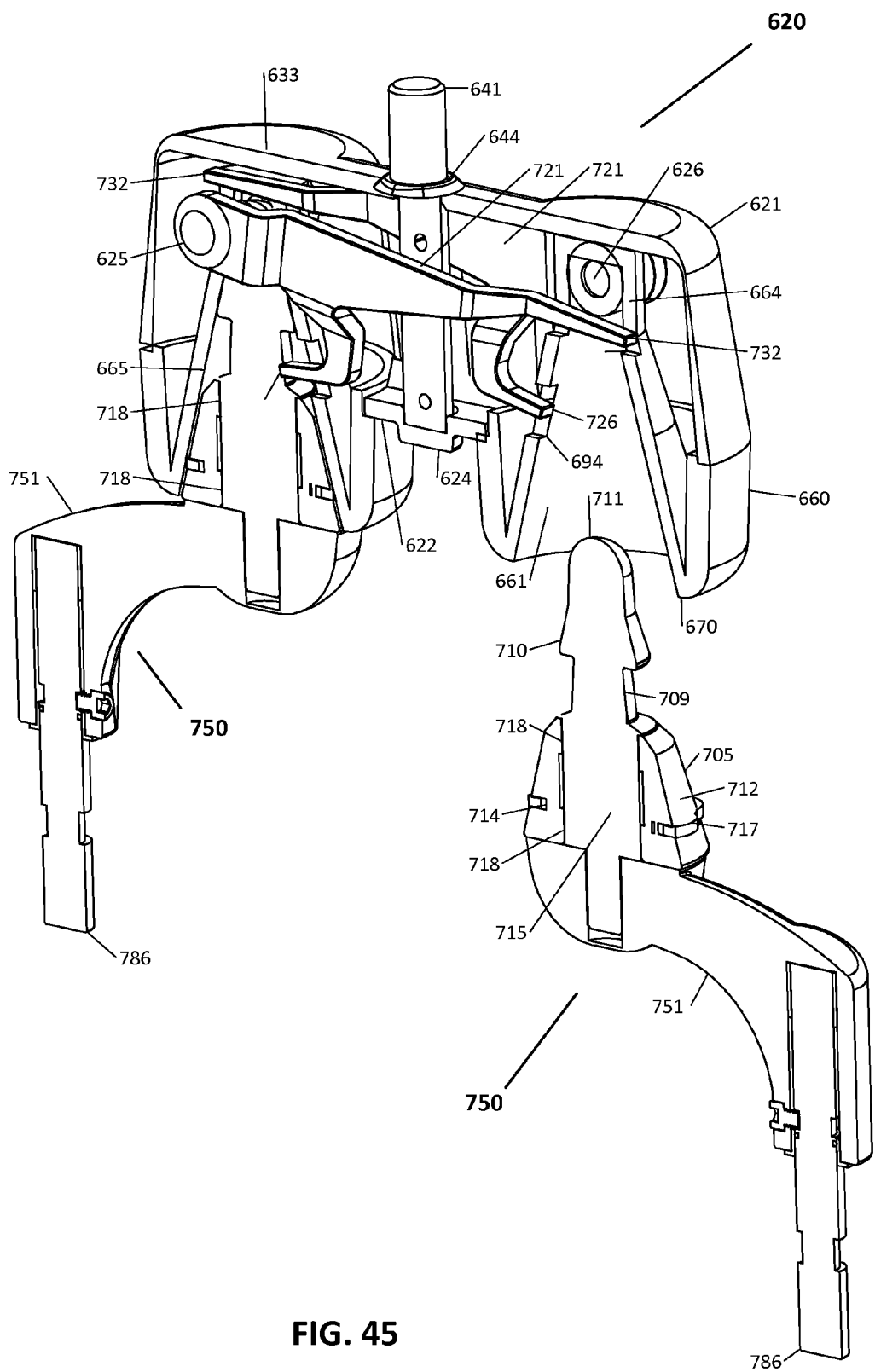
FIG. 45 is a cross sectional view of the transfer device and system.

As shown in FIG. 45, a cone arm 750 is attached to a stationary or mobile support platform. Cone arm 750 comprises arm structure 751, preferably an aluminum casting with, at its proximal end, a shaft 786 and at its distal end a docking cone 700 that is configured for docking engagement with docking cups 660 of transfer device 620. A spine 715 comprises upper cone 710, cone tip 711, inner bearing surface 718, and security engagement notch 709 and is attached to arm structure 751. As described above, the docking cone 700 has a security engagement notch 709 that cooperates with security latch 726 of security lever 721 to prevent or enable retention of docking cone 700, as the case may be, from docking cup 660.

It can also be seen in FIG. 41 that the security lever 721 has an offset 739 therein that creates a spaced apart relation that allows support post 641 to sit in the space created between the security levers 721. As a result, support post 641 can be positioned low in the transfer device 620 to achieve a low overall profile 650 of the transfer device 620 to accommodate attachment of more medical apparatus to the equipment support structure 200.

Turning now to FIG. 45, an alternate arrangement of cone arm 150 and docking cone 100 is shown. Rotation of transfer device 20 about docking cone 100 tends to allow the uncontrolled rotation, or swing-out, of the transfer device during transport. To prevent said swing-out rotation, revolving cone 705 is configured to rotate about spine 715. The inner bearing surface 718 is in contact with spine 715 and may optionally be coated with damping grease to slow and control the rotation of revolving cone 705 relative to spine 715. However, the use of alternative damping means other than grease is within the scope of this specification.

A groove 714 provided in the outer bearing surface 712 of revolving cone 705 is filled with a friction material 717 that extends outwardly to contact inner conical surface 665 of docking cup 660. When transfer device 620 is received onto revolving cone 705, friction material 717 engages the inner conical surface 665 of docking cup 660 to prevent rotation of the transfer device 620 relative to outer bearing surface 712 of revolving cone 705. This engagement transfers the rotation of the transfer device 620 to the rotation-controlled interface between the inner bearing surface 718 and spine 715, thereby effectively controlling rotation and swing-out of the overall transfer device 620.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described.

That which is claimed is:

1. A method of using a transfer system, the method comprising:
    obtaining a transfer system, the transfer system comprising:
    a first support platform;
    a first docking cone fixedly attached to and supported by the first support
    platform, the first docking cone comprising a tip and defining a docking cone axis, the docking cone axis of the first docking cone oriented with a vertical axis, and the tip of the first docking cone pointed upward; and
    a transfer device defining a first docking cup, the first docking cup defining a
    conical cavity facing downward, the transfer device comprising a security mechanism comprising a first security lever and a second security lever, the transfer device as assembled defining no upward-facing cavities;
    positioning the first docking cone below the first docking cup of a transfer device of the transfer system before inserting the first docking cone into the first docking cup;
    inserting the first docking cone into the conical cavity of the first docking cup of the transfer device of the transfer system; and
    automatically locking the first docking cone within the first docking cup by the security mechanism of the transfer device by inserting the first docking cone within the first docking cup to automatically engage a one of the first security lever and the second security lever of the security mechanism with a security notch defined in the first docking cone.

2. The method of claim 1, wherein the first support platform is a mobile support platform.

3. The method of claim 1, wherein positioning the first docking cone below the first docking cup comprises aligning the docking cone axis of the first docking cone with the first docking cup.

4. The method of claim 3, wherein aligning the docking cone axis of the first docking cone with the first docking cup comprises moving the first support platform.

5. The method of claim 1, wherein the docking cone axis of the first docking cone is misaligned with an axis of the first docking cup while inserting the first docking cone into the first docking cup.

6. The method of claim 1, wherein the transfer device is configured to rotate 360 degrees about the first docking cone with the first docking cone docked inside the first docking cup.

7. The method of claim 1, wherein inserting the first docking cone into the first docking cup comprises raising the first docking cone until the first docking cone engages the first docking cup.

8. The method of claim 1, further comprising supporting the weight of the transfer device with the first docking cone.

9. The method of claim 1, further comprising inserting a second docking cone of the transfer system into a second docking cup of the transfer device.

10. The method of claim 9, wherein fully inserting the second docking cone into the second docking cup unlocks the first docking cone from the first docking cup.

11. A method of using a transfer system, the method comprising:
    obtaining a transfer system, the transfer system comprising:
    a first support platform;
    a second support platform;
    a first docking cone fixedly attached to and supported by the first support platform, the first docking cone comprising a tip and defining a docking cone axis, the docking cone axis of the first docking cone oriented with a vertical axis, and the tip of the first docking cone pointed upward;
    a second docking cone fixedly attached to and supported by the second support platform, the second docking cone comprising a tip and defining a docking cone axis, the docking cone axis of the second docking cone oriented with a vertical axis, and the tip of the second docking cone pointed upward;
    a transfer device defining a first docking cup and a second docking cup, each of the first docking cup and the second docking cup defining a conical cavity facing downward, the transfer device comprising a security mechanism comprising a first security lever and a second security lever;
    locking the first docking cone within the downward-facing conical cavity of the first docking cup of the transfer device of the transfer system by the security mechanism of the transfer device, the security mechanism and the tip of the first docking cone housed within the first docking cup;
    automatically releasing the security mechanism of the transfer device from locking engagement with the first docking cone by engaging the second docking cone within the downward-facing conical cavity of the second docking cup of the transfer device, the tip of the second docking cone housed within the second docking cup; and
    locking the second docking cone within the second docking cup of the transfer device by moving the second docking cone upward relative to the first docking cone or moving the first docking cone downward relative to the second docking cone.

12. The method of claim 11, wherein the second support platform is a mobile support platform.

13. The method of claim 12, further comprising locking the second docking cone in place relative to the mobile support platform.

14. The method of claim 13, wherein locking the second docking cone in place relative to the mobile support platform comprises securing the second docking cone against rotation about the mobile support platform.

15. The method of claim 11, wherein unlocking the first docking cone from the transfer device comprises moving the transfer device in a vertical direction relative to the first docking cone to remove the transfer device from the first docking cone.

16. The method of claim 15, wherein removing the transfer device from the first docking cone locks the second docking cup in the second docking cup.

17. The method of claim 11, wherein the security mechanism includes a first security lever and a second security lever, the method further comprising engaging the first docking cone with the first security lever and engaging the second docking cone with the second security lever.

18. The method of claim 17, further comprising:

disengaging a security latch of the first security lever from a security notch of the first docking cone when the second docking cone is fully received within the second docking cup; and disengaging a security latch of the second security lever from a security notch of the second docking cone when the first docking cone is fully received within the first docking cup.

19. The method of claim 17, wherein each of the first security lever and the second security lever comprises a cone feeler, the method further comprising pivoting the first security lever from a first secured cone position to a second released cone position when the cone feeler of the first security lever is displaced by the tip of the second docking cone.

* * * * *